(12) United States Patent
Marczyk

(10) Patent No.: US 8,348,127 B2
(45) Date of Patent: Jan. 8, 2013

(54) SURGICAL FASTENER APPLYING APPARATUS

(75) Inventor: Stanislaw Marczyk, Stratford, CT (US)

(73) Assignee: Covidien LP, Mansfield, MA (US)

( * ) Notice: Subject to any disclaimer, the term of this patent is extended or adjusted under 35 U.S.C. 154(b) by 182 days.

(21) Appl. No.: 12/755,590

(22) Filed: Apr. 7, 2010

(65) Prior Publication Data

US 2011/0248064 A1 Oct. 13, 2011

(51) Int. Cl.
*A61B 17/04* (2006.01)
*A61B 17/10* (2006.01)

(52) U.S. Cl. ............... 227/177.1; 227/179.1; 606/219

(58) Field of Classification Search .... 227/175.1–182.1; 606/176.1, 139, 219, 52, 206, 142
See application file for complete search history.

(56) References Cited

U.S. PATENT DOCUMENTS

| | | | |
|---|---|---|---|
| 3,079,606 A | 3/1963 | Bobrov et al. | |
| 3,335,620 A * | 8/1967 | Vertut | 74/501.6 |
| 3,490,675 A | 1/1970 | Green et al. | |
| 3,504,838 A * | 4/1970 | Cairatti | 227/89 |
| 3,777,538 A | 12/1973 | Weatherly et al. | |
| 3,882,854 A | 5/1975 | Hulka et al. | |
| 4,027,510 A | 6/1977 | Hiltebrandt | |
| 4,086,926 A | 5/1978 | Green et al. | |
| 4,244,372 A | 1/1981 | Kapitanov et al. | |
| 4,429,695 A | 2/1984 | Green | |
| 4,505,414 A | 3/1985 | Filipi | |
| 4,520,817 A | 6/1985 | Green | |
| 4,589,413 A | 5/1986 | Malyshev et al. | |
| 4,596,351 A | 6/1986 | Fedotov et al. | |
| 4,602,634 A | 7/1986 | Barkley | |
| 4,605,001 A * | 8/1986 | Rothfuss et al. | 227/178.1 |
| 4,608,981 A | 9/1986 | Rothfuss et al. | |
| 4,610,383 A | 9/1986 | Rothfuss et al. | |
| 4,633,861 A | 1/1987 | Chow et al. | |
| 4,633,874 A | 1/1987 | Chow et al. | |
| 4,671,445 A | 6/1987 | Barker et al. | |
| 4,700,703 A | 10/1987 | Resnick et al. | |
| 4,703,887 A | 11/1987 | Clanton et al. | |
| 4,728,020 A | 3/1988 | Green et al. | |
| 4,752,024 A | 6/1988 | Green et al. | |
| 4,784,137 A | 11/1988 | Kulik et al. | |
| 4,863,088 A | 9/1989 | Redmond et al. | |
| 4,869,415 A | 9/1989 | Fox | |
| 4,892,244 A | 1/1990 | Fox et al. | |
| 4,930,674 A * | 6/1990 | Barak | 227/179.1 |
| 4,955,959 A | 9/1990 | Tompkins et al. | |

(Continued)

FOREIGN PATENT DOCUMENTS

AU 5476586 9/1986

(Continued)

*Primary Examiner* — Robert Long

(57) ABSTRACT

A surgical fastener cartridge is provided and includes a cartridge body having a plurality of surgical fasteners operatively disposed therein. An actuation mechanism is housed within the cartridge body and includes a plurality of pushers operably associated with the plurality of surgical fasteners. The actuation mechanism includes a plurality of pivotably connected link assemblies. Each link assembly being pivotably engaged with a corresponding bottom surface associated with each the pushers and a corresponding top surface associated with an internal channel housing and operably coupled to one another. The actuation mechanism includes an activation structure configured to move each of the link assemblies and sequentially cause each of the link assemblies to move through a succession of motions within the cartridge body, such that the link assemblies cause the corresponding pusher to contact and, subsequently, sequentially eject the associated surgical fastener towards the depression in the anvil.

11 Claims, 13 Drawing Sheets

U.S. PATENT DOCUMENTS

| | | | |
|---|---|---|---|
| 4,978,049 A | 12/1990 | Green | |
| 4,991,764 A | 2/1991 | Mericle | |
| 5,014,899 A | 5/1991 | Presty et al. | |
| 5,031,814 A | 7/1991 | Tompkins et al. | |
| 5,040,715 A | 8/1991 | Green et al. | |
| 5,065,929 A | 11/1991 | Schulze et al. | |
| 5,071,430 A | 12/1991 | deSalis et al. | |
| 5,074,454 A | 12/1991 | Peters | |
| 5,083,695 A | 1/1992 | Foslien et al. | |
| 5,084,057 A | 1/1992 | Green et al. | |
| 5,106,008 A | 4/1992 | Tompkins et al. | |
| 5,111,987 A | 5/1992 | Moeinzadeh et al. | |
| 5,129,570 A | 7/1992 | Schulze et al. | |
| 5,141,144 A | 8/1992 | Foslien et al. | |
| 5,156,315 A | 10/1992 | Green et al. | |
| 5,156,614 A | 10/1992 | Green et al. | |
| 5,163,943 A | 11/1992 | Mohiuddin et al. | |
| 5,170,925 A | 12/1992 | Madden et al. | |
| 5,171,247 A | 12/1992 | Hughetti et al. | |
| 5,173,133 A | 12/1992 | Morin et al. | |
| 5,180,092 A | 1/1993 | Crainich | |
| 5,188,274 A | 2/1993 | Moeinzadeh et al. | |
| 5,188,636 A * | 2/1993 | Fedotov | 606/144 |
| 5,220,928 A | 6/1993 | Oddsen et al. | |
| 5,221,036 A | 6/1993 | Takase | |
| 5,242,457 A | 9/1993 | Akopov et al. | |
| 5,246,156 A | 9/1993 | Rothfuss et al. | |
| 5,253,793 A | 10/1993 | Green et al. | |
| 5,263,629 A | 11/1993 | Trumbull et al. | |
| RE34,519 E | 1/1994 | Fox et al. | |
| 5,275,323 A | 1/1994 | Schulze et al. | |
| 5,282,807 A | 2/1994 | Knoepfler | |
| 5,289,963 A | 3/1994 | McGarry et al. | |
| 5,307,976 A | 5/1994 | Olson et al. | |
| 5,308,576 A | 5/1994 | Green et al. | |
| 5,312,023 A | 5/1994 | Green et al. | |
| 5,318,221 A | 6/1994 | Green et al. | |
| 5,326,013 A | 7/1994 | Green et al. | |
| 5,328,077 A | 7/1994 | Lou | |
| 5,330,486 A | 7/1994 | Wilk | |
| 5,332,142 A | 7/1994 | Robinson et al. | |
| 5,336,232 A | 8/1994 | Green et al. | |
| 5,344,061 A | 9/1994 | Crainich | |
| 5,352,238 A | 10/1994 | Green et al. | |
| 5,356,064 A | 10/1994 | Green et al. | |
| 5,358,506 A | 10/1994 | Green et al. | |
| 5,364,001 A | 11/1994 | Bryan | |
| 5,364,002 A | 11/1994 | Green et al. | |
| 5,364,003 A | 11/1994 | Williamson, IV | |
| 5,366,133 A | 11/1994 | Geiste | |
| 5,376,095 A | 12/1994 | Ortiz | |
| 5,379,933 A | 1/1995 | Green et al. | |
| 5,381,943 A | 1/1995 | Allen et al. | |
| 5,382,255 A | 1/1995 | Castro et al. | |
| 5,383,880 A | 1/1995 | Hooven | |
| 5,395,033 A | 3/1995 | Byrne et al. | |
| 5,395,034 A | 3/1995 | Allen et al. | |
| 5,397,046 A | 3/1995 | Savage et al. | |
| 5,397,324 A | 3/1995 | Carroll et al. | |
| 5,405,072 A | 4/1995 | Zlock et al. | |
| 5,407,293 A | 4/1995 | Crainich | |
| 5,413,268 A | 5/1995 | Green et al. | |
| 5,415,334 A | 5/1995 | Williamson, IV et al. | |
| 5,415,335 A | 5/1995 | Knodell, Jr. | |
| 5,417,361 A | 5/1995 | Williamson, IV | |
| 5,423,471 A | 6/1995 | Mastri et al. | |
| 5,425,745 A | 6/1995 | Green et al. | |
| 5,431,322 A | 7/1995 | Green et al. | |
| 5,431,323 A | 7/1995 | Smith et al. | |
| 5,433,721 A | 7/1995 | Hooven et al. | |
| 5,441,193 A | 8/1995 | Gravener | |
| 5,445,304 A | 8/1995 | Plyley et al. | |
| 5,447,265 A | 9/1995 | Vidal et al. | |
| 5,452,837 A | 9/1995 | Williamson, IV et al. | |
| 5,456,401 A | 10/1995 | Green et al. | |
| 5,464,300 A | 11/1995 | Crainich | |
| 5,465,895 A | 11/1995 | Knodel et al. | |
| 5,467,911 A | 11/1995 | Tsuruta et al. | |
| 5,470,007 A | 11/1995 | Plyley et al. | |
| 5,470,010 A | 11/1995 | Rothfuss et al. | |
| 5,472,132 A | 12/1995 | Savage et al. | |
| 5,474,566 A | 12/1995 | Alesi et al. | |
| 5,476,206 A | 12/1995 | Green et al. | |
| 5,478,003 A | 12/1995 | Green et al. | |
| 5,480,089 A | 1/1996 | Blewett | |
| 5,482,197 A | 1/1996 | Green et al. | |
| 5,484,095 A | 1/1996 | Green et al. | |
| 5,484,451 A | 1/1996 | Akopov et al. | |
| 5,485,947 A | 1/1996 | Olson et al. | |
| 5,485,952 A | 1/1996 | Fontayne | |
| 5,486,185 A | 1/1996 | Freitas et al. | |
| 5,487,499 A | 1/1996 | Sorrentino et al. | |
| 5,487,500 A | 1/1996 | Knodel et al. | |
| 5,489,058 A | 2/1996 | Plyley et al. | |
| 5,490,856 A | 2/1996 | Person et al. | |
| 5,497,933 A | 3/1996 | DeFonzo et al. | |
| 5,501,689 A | 3/1996 | Green et al. | |
| 5,505,363 A | 4/1996 | Green et al. | |
| 5,507,426 A | 4/1996 | Young et al. | |
| 5,518,163 A | 5/1996 | Hooven | |
| 5,518,164 A | 5/1996 | Hooven | |
| 5,529,235 A | 6/1996 | Boiarski et al. | |
| 5,531,744 A | 7/1996 | Nardella et al. | |
| 5,535,934 A | 7/1996 | Boiarski et al. | |
| 5,535,935 A | 7/1996 | Vidal et al. | |
| 5,535,937 A | 7/1996 | Boiarski et al. | |
| 5,540,375 A | 7/1996 | Bolanos et al. | |
| 5,542,594 A | 8/1996 | McKean et al. | |
| 5,547,474 A * | 8/1996 | Kloeckl et al. | 606/143 |
| 5,549,628 A | 8/1996 | Cooper et al. | |
| 5,551,622 A | 9/1996 | Yoon | |
| 5,553,765 A | 9/1996 | Knodel et al. | |
| 5,554,164 A | 9/1996 | Wilson et al. | |
| 5,554,169 A | 9/1996 | Green et al. | |
| 5,560,530 A | 10/1996 | Bolanos et al. | |
| 5,560,532 A | 10/1996 | DeFonzo et al. | |
| 5,562,239 A | 10/1996 | Boiarski et al. | |
| 5,562,241 A | 10/1996 | Knodel et al. | |
| 5,562,682 A | 10/1996 | Oberlin et al. | |
| 5,562,701 A | 10/1996 | Huitema et al. | |
| 5,564,615 A | 10/1996 | Bishop et al. | |
| 5,571,116 A | 11/1996 | Bolanos et al. | |
| 5,573,169 A | 11/1996 | Green et al. | |
| 5,573,543 A | 11/1996 | Akopov et al. | |
| 5,575,799 A | 11/1996 | Bolanos et al. | |
| 5,575,803 A | 11/1996 | Cooper et al. | |
| 5,577,654 A | 11/1996 | Bishop | |
| 5,579,107 A | 11/1996 | Wright et al. | |
| 5,584,425 A | 12/1996 | Savage et al. | |
| 5,586,711 A | 12/1996 | Plyley et al. | |
| 5,588,580 A | 12/1996 | Paul et al. | |
| 5,588,581 A | 12/1996 | Conlon et al. | |
| 5,597,107 A | 1/1997 | Knodel et al. | |
| 5,601,224 A | 2/1997 | Bishop et al. | |
| 5,607,095 A | 3/1997 | Smith et al. | |
| 5,615,820 A | 4/1997 | Viola | |
| 5,618,291 A | 4/1997 | Thompson et al. | |
| 5,624,452 A | 4/1997 | Yates | |
| 5,626,587 A | 5/1997 | Bishop et al. | |
| 5,628,446 A | 5/1997 | Geiste et al. | |
| 5,630,539 A | 5/1997 | Plyley et al. | |
| 5,630,540 A | 5/1997 | Blewett | |
| 5,630,541 A | 5/1997 | Williamson, IV et al. | |
| 5,632,432 A | 5/1997 | Schulze et al. | |
| 5,634,584 A | 6/1997 | Okorocha et al. | |
| 5,636,780 A | 6/1997 | Green et al. | |
| 5,645,209 A | 7/1997 | Green et al. | |
| 5,647,526 A | 7/1997 | Green et al. | |
| 5,651,491 A | 7/1997 | Heaton et al. | |
| 5,653,373 A | 8/1997 | Green et al. | |
| 5,653,374 A | 8/1997 | Young et al. | |
| 5,653,721 A | 8/1997 | Knodel et al. | |
| 5,655,698 A | 8/1997 | Yoon | |
| 5,657,921 A | 8/1997 | Young et al. | |
| 5,658,300 A | 8/1997 | Bito et al. | |
| 5,662,258 A | 9/1997 | Knodel et al. | |
| 5,662,259 A | 9/1997 | Yoon | |

| Patent No. | Date | Inventor(s) | Patent No. | Date | Inventor(s) |
|---|---|---|---|---|---|
| 5,662,260 A | 9/1997 | Yoon | 6,004,335 A | 12/1999 | Vaitekunas et al. |
| 5,662,662 A | 9/1997 | Bishop et al. | 6,010,054 A | 1/2000 | Johnson et al. |
| 5,662,666 A | 9/1997 | Onuki et al. | 6,032,849 A | 3/2000 | Mastri et al. |
| 5,665,085 A | 9/1997 | Nardella | 6,045,560 A | 4/2000 | McKean et al. |
| 5,667,517 A | 9/1997 | Hooven | 6,063,097 A | 5/2000 | Oi et al. |
| 5,669,544 A | 9/1997 | Schulze et al. | 6,079,606 A | 6/2000 | Milliman et al. |
| 5,673,840 A | 10/1997 | Schulze et al. | 6,099,551 A | 8/2000 | Gabbay |
| 5,673,841 A | 10/1997 | Schulze et al. | 6,109,500 A | 8/2000 | Alli et al. |
| 5,673,842 A | 10/1997 | Bittner et al. | 6,131,789 A | 10/2000 | Schulze et al. |
| 5,676,674 A | 10/1997 | Bolanos et al. | 6,131,790 A | 10/2000 | Piraka |
| 5,680,981 A | 10/1997 | Mililli et al. | 6,155,473 A | 12/2000 | Tompkins et al. |
| 5,680,982 A | 10/1997 | Schulze et al. | 6,197,017 B1 | 3/2001 | Brock et al. |
| 5,690,269 A | 11/1997 | Bolanos et al. | 6,202,914 B1 | 3/2001 | Geiste et al. |
| 5,692,668 A | 12/1997 | Schulze et al. | 6,241,139 B1 | 6/2001 | Milliman et al. |
| 5,697,542 A | 12/1997 | Knodel et al. | 6,250,532 B1 | 6/2001 | Green et al. |
| 5,702,409 A | 12/1997 | Rayburn et al. | 6,264,086 B1 | 7/2001 | McGuckin, Jr. |
| 5,704,534 A | 1/1998 | Huitema et al. | 6,264,087 B1 | 7/2001 | Whitman |
| 5,706,997 A | 1/1998 | Green et al. | 6,269,977 B1 | 8/2001 | Moore |
| 5,709,334 A | 1/1998 | Sorrentino et al. | 6,279,809 B1 | 8/2001 | Nicolo |
| 5,711,472 A | 1/1998 | Bryan | 6,315,183 B1 | 11/2001 | Piraka |
| 5,713,505 A | 2/1998 | Huitema | 6,315,184 B1 | 11/2001 | Whitman |
| 5,715,988 A | 2/1998 | Palmer | 6,325,810 B1 | 12/2001 | Hamilton et al. |
| 5,716,366 A | 2/1998 | Yates | 6,330,965 B1 | 12/2001 | Milliman et al. |
| 5,718,359 A | 2/1998 | Palmer | 6,391,038 B2 | 5/2002 | Vargas et al. |
| 5,725,536 A | 3/1998 | Oberlin et al. | 6,398,797 B2 | 6/2002 | Bombard et al. |
| 5,725,554 A | 3/1998 | Simon et al. | 6,436,097 B1 | 8/2002 | Nardella |
| 5,728,110 A | 3/1998 | Vidal et al. | 6,439,446 B1 | 8/2002 | Perry et al. |
| 5,732,806 A | 3/1998 | Foshee et al. | 6,443,973 B1 | 9/2002 | Whitman |
| 5,735,848 A | 4/1998 | Yates et al. | 6,463,623 B2 | 10/2002 | Ahn et al. |
| 5,743,456 A | 4/1998 | Jones et al. | 6,478,804 B2 | 11/2002 | Vargas et al. |
| 5,749,893 A | 5/1998 | Vidal et al. | 6,488,196 B1 | 12/2002 | Fenton, Jr. |
| 5,752,644 A | 5/1998 | Bolanos et al. | 6,503,257 B2 | 1/2003 | Grant et al. |
| 5,762,255 A | 6/1998 | Chrisman et al. | 6,505,768 B2 | 1/2003 | Whitman |
| 5,762,256 A | 6/1998 | Mastri et al. | 6,544,274 B2 | 4/2003 | Danitz et al. |
| 5,769,303 A | 6/1998 | Knodel et al. | 6,554,844 B2 | 4/2003 | Lee et al. |
| 5,769,892 A | 6/1998 | Kingwell | 6,565,554 B1 | 5/2003 | Niemeyer |
| 5,772,099 A | 6/1998 | Gravener | 6,587,750 B2 | 7/2003 | Gerbi et al. |
| 5,772,673 A | 6/1998 | Cuny et al. | 6,592,597 B2 | 7/2003 | Grant et al. |
| 5,779,130 A | 7/1998 | Alesi et al. | 6,594,552 B1 | 7/2003 | Nowlin et al. |
| 5,779,131 A | 7/1998 | Knodel et al. | 6,602,252 B2 | 8/2003 | Mollenauer |
| 5,779,132 A | 7/1998 | Knodel et al. | 6,612,053 B2 | 9/2003 | Liao |
| 5,782,396 A | 7/1998 | Mastri et al. | 6,619,529 B2 | 9/2003 | Green et al. |
| 5,782,397 A | 7/1998 | Koukline | 6,644,532 B2 | 11/2003 | Green et al. |
| 5,782,834 A | 7/1998 | Lucey et al. | 6,656,193 B2 | 12/2003 | Grant et al. |
| 5,785,232 A | 7/1998 | Vidal et al. | 6,669,073 B2 | 12/2003 | Milliman et al. |
| 5,797,536 A | 8/1998 | Smith et al. | 6,681,978 B2 | 1/2004 | Geiste et al. |
| 5,797,537 A | 8/1998 | Oberlin et al. | 6,698,643 B2 | 3/2004 | Whitman |
| 5,797,538 A * | 8/1998 | Heaton et al. ............ 227/176.1 | 6,716,232 B1 | 4/2004 | Vidal et al. |
| 5,810,811 A | 9/1998 | Yates et al. | 6,722,552 B2 | 4/2004 | Fenton, Jr. |
| 5,810,855 A | 9/1998 | Rayburn et al. | 6,731,473 B2 | 5/2004 | Li et al. |
| 5,814,055 A | 9/1998 | Knodel et al. | 6,755,338 B2 | 6/2004 | Hahnen et al. |
| 5,814,057 A | 9/1998 | Oi et al. | 6,783,524 B2 | 8/2004 | Anderson et al. |
| 5,816,471 A | 10/1998 | Plyley et al. | 6,786,382 B1 | 9/2004 | Hoffman |
| 5,817,109 A | 10/1998 | McGarry et al. | 6,808,262 B2 | 10/2004 | Chapoy et al. |
| 5,820,009 A | 10/1998 | Melling et al. | 6,817,509 B2 | 11/2004 | Geiste et al. |
| 5,823,066 A | 10/1998 | Huitema et al. | 6,830,174 B2 | 12/2004 | Hillstead et al. |
| 5,826,776 A * | 10/1998 | Schulze et al. ............ 227/176.1 | 6,835,199 B2 | 12/2004 | McGuckin, Jr. et al. |
| 5,829,662 A | 11/1998 | Allen et al. | 6,837,895 B2 * | 1/2005 | Mayenberger ................ 606/142 |
| 5,833,695 A | 11/1998 | Yoon | 6,843,403 B2 | 1/2005 | Whitman |
| 5,836,147 A | 11/1998 | Schnipke | RE38,708 E | 3/2005 | Bolanos et al. |
| 5,862,972 A | 1/1999 | Green et al. | 6,877,647 B2 | 4/2005 | Greeen et al. |
| 5,865,361 A | 2/1999 | Milliman et al. | 6,879,880 B2 | 4/2005 | Nowlin et al. |
| 5,871,135 A | 2/1999 | Williamson IV et al. | 6,889,116 B2 | 5/2005 | Jinno |
| 5,873,873 A | 2/1999 | Smith et al. | 6,905,057 B2 | 6/2005 | Swayze et al. |
| 5,878,938 A | 3/1999 | Bittner et al. | 6,953,138 B1 | 10/2005 | Dworak et al. |
| 5,893,506 A | 4/1999 | Powell | 6,953,139 B2 | 10/2005 | Milliman et al. |
| 5,894,979 A | 4/1999 | Powell | 6,959,852 B2 | 11/2005 | Shelton, IV et al. |
| 5,897,562 A * | 4/1999 | Bolanos et al. ............ 606/139 | 6,962,594 B1 | 11/2005 | Thevenet |
| 5,901,895 A * | 5/1999 | Heaton et al. ............ 227/176.1 | 6,964,363 B2 | 11/2005 | Wales et al. |
| 5,911,352 A | 6/1999 | Racenet et al. | 6,978,921 B2 | 12/2005 | Shelton, IV et al. |
| 5,911,353 A | 6/1999 | Bolanos et al. | 6,981,628 B2 | 1/2006 | Wales |
| 5,918,791 A | 7/1999 | Sorrentino et al. | 6,986,451 B1 | 1/2006 | Mastri et al. |
| 5,919,198 A | 7/1999 | Graves, Jr. et al. | 6,988,649 B2 | 1/2006 | Shelton, IV et al. |
| 5,922,001 A | 7/1999 | Yoon | 6,991,627 B2 | 1/2006 | Madhani et al. |
| 5,931,847 A | 8/1999 | Bittner et al. | 6,994,714 B2 | 2/2006 | Vargas et al. |
| 5,941,442 A | 8/1999 | Geiste et al. | 7,000,818 B2 | 2/2006 | Shelton, IV et al. |
| 5,954,259 A | 9/1999 | Viola et al. | 7,000,819 B2 | 2/2006 | Swayze et al. |
| 5,980,510 A | 11/1999 | Tsonton et al. | 7,032,799 B2 | 4/2006 | Viola et al. |
| 5,988,479 A | 11/1999 | Palmer | 7,044,352 B2 | 5/2006 | Shelton, IV et al. |

| Patent No. | Kind | Date | Inventor(s) |
|---|---|---|---|
| 7,044,353 | B2 | 5/2006 | Mastri et al. |
| 7,055,730 | B2 | 6/2006 | Ehrenfels et al. |
| 7,055,731 | B2 | 6/2006 | Shelton, IV et al. |
| 7,059,508 | B2 | 6/2006 | Shelton, IV et al. |
| 7,070,083 | B2 | 7/2006 | Jankowski |
| 7,083,075 | B2 | 8/2006 | Swayze et al. |
| 7,097,089 | B2 | 8/2006 | Marczyk |
| 7,111,769 | B2 | 9/2006 | Wales et al. |
| 7,114,642 | B2 | 10/2006 | Whitman |
| 7,121,446 | B2 | 10/2006 | Arad et al. |
| 7,128,253 | B2 | 10/2006 | Mastri et al. |
| 7,128,254 | B2 | 10/2006 | Shelton, IV et al. |
| 7,140,527 | B2 | 11/2006 | Ehrenfels et al. |
| 7,140,528 | B2 | 11/2006 | Shelton, IV |
| 7,143,923 | B2 | 12/2006 | Shelton, IV et al. |
| 7,143,924 | B2 | 12/2006 | Scirica et al. |
| 7,143,925 | B2 | 12/2006 | Shelton, IV et al. |
| 7,143,926 | B2 | 12/2006 | Shelton, IV et al. |
| 7,147,138 | B2 | 12/2006 | Shelton, IV |
| 7,159,750 | B2 | 1/2007 | Racenet et al. |
| 7,172,104 | B2 | 2/2007 | Scirica et al. |
| 7,188,758 | B2 | 3/2007 | Viola et al. |
| 7,207,471 | B2 | 4/2007 | Heinrich et al. |
| 7,213,736 | B2 | 5/2007 | Wales et al. |
| 7,225,963 | B2 | 6/2007 | Scirica |
| 7,225,964 | B2 | 6/2007 | Mastri et al. |
| 7,238,195 | B2 | 7/2007 | Viola |
| 7,246,734 | B2 | 7/2007 | Shelton, IV |
| 7,258,262 | B2 | 8/2007 | Mastri et al. |
| 7,278,562 | B2 | 10/2007 | Mastri et al. |
| 7,278,563 | B1 | 10/2007 | Green |
| 7,287,682 | B1 | 10/2007 | Ezzat et al. |
| 7,293,685 | B2 | 11/2007 | Ehrenfels et al. |
| 7,296,724 | B2 | 11/2007 | Green et al. |
| 7,296,772 | B2 | 11/2007 | Wang |
| 7,300,444 | B1 | 11/2007 | Nielsen et al. |
| 7,303,108 | B2 | 12/2007 | Shelton, IV |
| 7,308,998 | B2 | 12/2007 | Mastri et al. |
| 7,328,828 | B2 | 2/2008 | Ortiz et al. |
| 7,328,829 | B2 | 2/2008 | Arad et al. |
| 7,354,447 | B2 | 4/2008 | Shelton, IV et al. |
| 7,357,287 | B2 | 4/2008 | Shelton, IV et al. |
| 7,364,061 | B2 | 4/2008 | Swayze et al. |
| 7,367,485 | B2 | 5/2008 | Shelton, IV et al. |
| 7,380,695 | B2 | 6/2008 | Doll et al. |
| 7,380,696 | B2 | 6/2008 | Shelton, IV et al. |
| 7,399,310 | B2 | 7/2008 | Edoga et al. |
| 7,401,720 | B1 | 7/2008 | Durrani |
| 7,404,508 | B2 | 7/2008 | Smith et al. |
| 7,404,509 | B2 | 7/2008 | Ortiz et al. |
| 7,407,074 | B2 | 8/2008 | Ortiz et al. |
| 7,407,077 | B2 | 8/2008 | Ortiz et al. |
| 7,407,078 | B2 | 8/2008 | Shelton, IV et al. |
| 7,416,101 | B2 | 8/2008 | Shelton, IV et al. |
| 7,419,080 | B2 | 9/2008 | Smith et al. |
| 7,419,495 | B2 | 9/2008 | Menn et al. |
| 7,422,139 | B2 | 9/2008 | Shelton, IV et al. |
| 7,431,189 | B2 | 10/2008 | Shelton, IV et al. |
| 7,434,715 | B2 | 10/2008 | Shelton, IV et al. |
| 7,434,717 | B2 | 10/2008 | Shelton, IV et al. |
| 7,438,208 | B2 | 10/2008 | Larson |
| 7,438,209 | B1 | 10/2008 | Hess et al. |
| 7,441,684 | B2 | 10/2008 | Shelton, IV et al. |
| 7,441,685 | B1 | 10/2008 | Boudreaux |
| 7,448,525 | B2 | 11/2008 | Shelton, IV et al. |
| 7,451,904 | B2 | 11/2008 | Shelton, IV |
| 7,455,208 | B2 | 11/2008 | Wales et al. |
| 7,458,494 | B2 | 12/2008 | Matsutani et al. |
| 7,461,767 | B2 | 12/2008 | Viola et al. |
| 7,462,185 | B1 | 12/2008 | Knodel |
| 7,464,846 | B2 | 12/2008 | Shelton, IV et al. |
| 7,464,848 | B2 | 12/2008 | Green et al. |
| 7,464,849 | B2 | 12/2008 | Shelton, IV et al. |
| 7,467,740 | B2 | 12/2008 | Shelton, IV et al. |
| 7,472,814 | B2 | 1/2009 | Mastri et al. |
| 7,472,815 | B2 | 1/2009 | Shelton, IV et al. |
| 7,472,816 | B2 | 1/2009 | Holsten et al. |
| 7,473,258 | B2 | 1/2009 | Clauson et al. |
| 7,481,347 | B2 | 1/2009 | Roy |
| 7,481,348 | B2 | 1/2009 | Marczyk |
| 7,481,349 | B2 | 1/2009 | Holsten et al. |
| 7,487,899 | B2 | 2/2009 | Shelton, IV et al. |
| 7,490,749 | B2 | 2/2009 | Schall et al. |
| 7,494,039 | B2 | 2/2009 | Racenet et al. |
| 7,500,979 | B2 | 3/2009 | Hueil et al. |
| 7,503,474 | B2 | 3/2009 | Hillstead et al. |
| 7,506,790 | B2 | 3/2009 | Shelton, IV |
| 7,510,107 | B2 | 3/2009 | Timm et al. |
| 7,513,408 | B2 | 4/2009 | Shelton, IV et al. |
| 7,516,877 | B2 * | 4/2009 | Aranyi ............... 227/176.1 |
| 7,517,356 | B2 | 4/2009 | Heinrich |
| 7,537,602 | B2 | 5/2009 | Whitman |
| 7,543,729 | B2 | 6/2009 | Ivanko |
| 7,543,730 | B1 | 6/2009 | Marczyk |
| 7,543,731 | B2 | 6/2009 | Green et al. |
| 7,556,185 | B2 | 7/2009 | Viola |
| 7,556,186 | B2 | 7/2009 | Milliman |
| 7,559,450 | B2 | 7/2009 | Wales et al. |
| 7,559,452 | B2 | 7/2009 | Wales et al. |
| 7,559,453 | B2 | 7/2009 | Heinrich et al. |
| 7,559,937 | B2 | 7/2009 | de la Torre et al. |
| 7,565,993 | B2 | 7/2009 | Milliman et al. |
| 7,568,603 | B2 | 8/2009 | Shelton, IV et al. |
| 7,568,604 | B2 | 8/2009 | Ehrenfels et al. |
| 7,571,845 | B2 | 8/2009 | Viola |
| 7,575,144 | B2 | 8/2009 | Ortiz et al. |
| 7,584,880 | B2 | 9/2009 | Racenet et al. |
| 7,588,175 | B2 | 9/2009 | Timm et al. |
| 7,588,176 | B2 | 9/2009 | Timm et al. |
| 7,588,177 | B2 | 9/2009 | Racenet |
| 7,597,229 | B2 | 10/2009 | Boudreaux et al. |
| 7,597,230 | B2 | 10/2009 | Racenet et al. |
| 7,604,150 | B2 | 10/2009 | Boudreaux |
| 7,604,151 | B2 | 10/2009 | Hess et al. |
| 7,607,557 | B2 | 10/2009 | Shelton, IV et al. |
| 7,611,038 | B2 | 11/2009 | Racenet et al. |
| 7,617,961 | B2 | 11/2009 | Viola |
| 7,624,902 | B2 | 12/2009 | Marczyk et al. |
| 7,624,903 | B2 | 12/2009 | Green et al. |
| 7,631,793 | B2 | 12/2009 | Rethy et al. |
| 7,631,794 | B2 | 12/2009 | Rethy et al. |
| 7,635,073 | B2 | 12/2009 | Heinrich |
| 7,635,074 | B2 | 12/2009 | Olson et al. |
| 7,635,373 | B2 | 12/2009 | Ortiz |
| 7,637,409 | B2 | 12/2009 | Marczyk |
| 7,637,410 | B2 | 12/2009 | Marczyk |
| 7,641,091 | B2 | 1/2010 | Olson et al. |
| 7,641,093 | B2 * | 1/2010 | Doll et al. ............... 227/175.4 |
| 7,641,095 | B2 * | 1/2010 | Viola ............... 227/176.1 |
| 7,644,848 | B2 | 1/2010 | Swayze et al. |
| 7,648,055 | B2 | 1/2010 | Marczyk |
| 7,651,017 | B2 | 1/2010 | Ortiz et al. |
| 7,654,431 | B2 | 2/2010 | Hueil et al. |
| 7,658,311 | B2 | 2/2010 | Boudreaux |
| 7,658,312 | B2 | 2/2010 | Vidal et al. |
| 7,665,646 | B2 | 2/2010 | Prommersberger |
| 7,665,647 | B2 | 2/2010 | Shelton, IV et al. |
| 7,669,746 | B2 | 3/2010 | Shelton, IV |
| 7,670,334 | B2 | 3/2010 | Hueil et al. |
| 7,673,780 | B2 | 3/2010 | Shelton, IV et al. |
| 7,673,781 | B2 | 3/2010 | Swayze et al. |
| 7,673,782 | B2 | 3/2010 | Hess et al. |
| 7,673,783 | B2 | 3/2010 | Morgan et al. |
| 7,678,121 | B1 | 3/2010 | Knodel |
| 7,681,772 | B2 | 3/2010 | Green et al. |
| 7,682,367 | B2 | 3/2010 | Shah et al. |
| 7,682,368 | B1 | 3/2010 | Bombard et al. |
| 7,690,547 | B2 | 4/2010 | Racenet et al. |
| 7,694,865 | B2 | 4/2010 | Scirica |
| 7,934,630 | B2 * | 5/2011 | Shelton et al. ............... 227/176.1 |
| 8,172,870 | B2 * | 5/2012 | Shipp ............... 606/205 |
| 2004/0007608 | A1 | 1/2004 | Ehrenfels et al. |
| 2004/0050902 | A1 | 3/2004 | Green et al. |
| 2004/0093029 | A1 | 5/2004 | Zubik et al. |
| 2004/0094597 | A1 | 5/2004 | Whitman |
| 2004/0108357 | A1 | 6/2004 | Milliman |
| 2004/0149802 | A1 | 8/2004 | Whitman |
| 2004/0173659 | A1 | 9/2004 | Green |

| | | | | | | |
|---|---|---|---|---|---|---|
| 2004/0199180 A1 | 10/2004 | Knodel et al. | | 2007/0045380 A1 | 3/2007 | Mastri et al. |
| 2004/0199181 A1 | 10/2004 | Knodel et al. | | 2007/0068989 A1 | 3/2007 | Shelton, IV |
| 2004/0232199 A1 | 11/2004 | Shelton, IV et al. | | 2007/0068990 A1 | 3/2007 | Shelton, IV et al. |
| 2004/0232200 A1 | 11/2004 | Shelton, IV et al. | | 2007/0073340 A1 | 3/2007 | Shelton, IV et al. |
| 2004/0232201 A1 | 11/2004 | Wenchell | | 2007/0073341 A1 | 3/2007 | Smith et al. |
| 2004/0243151 A1 | 12/2004 | Demmy | | 2007/0075114 A1 | 4/2007 | Shelton, IV et al. |
| 2004/0267310 A1 | 12/2004 | Racenet | | 2007/0075115 A1 | 4/2007 | Olson et al. |
| 2004/0267311 A1 | 12/2004 | Viola et al. | | 2007/0075116 A1 | 4/2007 | Whitman |
| 2005/0006429 A1 | 1/2005 | Wales | | 2007/0083233 A1 | 4/2007 | Ortiz et al. |
| 2005/0006430 A1 | 1/2005 | Wales | | 2007/0083234 A1 | 4/2007 | Shelton, IV et al. |
| 2005/0006431 A1 | 1/2005 | Shelton, IV et al. | | 2007/0084896 A1 | 4/2007 | Doll et al. |
| 2005/0006432 A1 | 1/2005 | Racenet | | 2007/0084897 A1 | 4/2007 | Shelton, IV et al. |
| 2005/0006433 A1 | 1/2005 | Milliman | | 2007/0084898 A1 | 4/2007 | Scirica |
| 2005/0006434 A1 | 1/2005 | Wales et al. | | 2007/0084899 A1 | 4/2007 | Taylor |
| 2005/0023324 A1 | 2/2005 | Doll et al. | | 2007/0102472 A1 | 5/2007 | Shelton, IV |
| 2005/0023325 A1 | 2/2005 | Gresham | | 2007/0102473 A1 | 5/2007 | Shelton, IV |
| 2005/0067457 A1 | 3/2005 | Shelton | | 2007/0102474 A1 | 5/2007 | Shelton, IV |
| 2005/0067458 A1 | 3/2005 | Swayze et al. | | 2007/0102475 A1 | 5/2007 | Ortiz et al. |
| 2005/0067459 A1 | 3/2005 | Swayze et al. | | 2007/0102476 A1 | 5/2007 | Shelton, IV |
| 2005/0067460 A1 | 3/2005 | Milliman | | 2007/0106317 A1 | 5/2007 | Shelton, IV |
| 2005/0070925 A1 | 3/2005 | Shelton, IV et al. | | 2007/0108252 A1 | 5/2007 | Racenet et al. |
| 2005/0070958 A1 | 3/2005 | Swayze et al. | | 2007/0114261 A1 | 5/2007 | Ortiz et al. |
| 2005/0072827 A1 | 4/2005 | Mollenauer | | 2007/0114262 A1 | 5/2007 | Mastri et al. |
| 2005/0082336 A1 | 4/2005 | Ivanko | | 2007/0119900 A1 | 5/2007 | Ehrenfels et al. |
| 2005/0103819 A1 | 5/2005 | Racenet | | 2007/0119901 A1 | 5/2007 | Ehrenfels et al. |
| 2005/0119669 A1 | 6/2005 | Demmy | | 2007/0125826 A1 | 6/2007 | Shelton, IV |
| 2005/0127131 A1 | 6/2005 | Mastri | | 2007/0125827 A1 | 6/2007 | Viola |
| 2005/0145671 A1 | 7/2005 | Viola | | 2007/0125828 A1 | 6/2007 | Rethy et al. |
| 2005/0159778 A1 | 7/2005 | Heinrich et al. | | 2007/0145095 A1 | 6/2007 | Heinrich et al. |
| 2005/0165415 A1 | 7/2005 | Wales | | 2007/0145096 A1 | 6/2007 | Viola et al. |
| 2005/0173490 A1 | 8/2005 | Shelton, IV | | 2007/0152014 A1 | 7/2007 | Gillum et al. |
| 2005/0178813 A1 | 8/2005 | Swayze et al. | | 2007/0158385 A1 | 7/2007 | Hueil et al. |
| 2005/0184121 A1 | 8/2005 | Heinrich | | 2007/0170225 A1 | 7/2007 | Shelton, IV et al. |
| 2005/0184123 A1 | 8/2005 | Scirica et al. | | 2007/0175947 A1 | 8/2007 | Ortiz et al. |
| 2005/0184124 A1 | 8/2005 | Scirica et al. | | 2007/0175948 A1 | 8/2007 | Scirica et al. |
| 2005/0184125 A1 | 8/2005 | Marczyk | | 2007/0175949 A1 | 8/2007 | Shelton, IV et al. |
| 2005/0184126 A1 | 8/2005 | Green et al. | | 2007/0175950 A1 | 8/2007 | Shelton, IV et al. |
| 2005/0189397 A1 | 9/2005 | Jankowski | | 2007/0175951 A1 | 8/2007 | Shelton, IV et al. |
| 2005/0192628 A1 | 9/2005 | Viola | | 2007/0175952 A1 | 8/2007 | Shelton, IV et al. |
| 2005/0216055 A1 | 9/2005 | Scirica et al. | | 2007/0175953 A1 | 8/2007 | Shelton, IV et al. |
| 2005/0230453 A1 | 10/2005 | Viola | | 2007/0175954 A1 | 8/2007 | Viola |
| 2005/0263562 A1 | 12/2005 | Shelton, IV et al. | | 2007/0175955 A1 | 8/2007 | Shelton, IV et al. |
| 2005/0279804 A1 | 12/2005 | Scirica et al. | | 2007/0175956 A1 | 8/2007 | Swayze et al. |
| 2006/0000867 A1 | 1/2006 | Shelton, IV et al. | | 2007/0175957 A1 | 8/2007 | Shelton, IV et al. |
| 2006/0000868 A1 | 1/2006 | Shelton, IV et al. | | 2007/0175958 A1 | 8/2007 | Shelton, IV et al. |
| 2006/0011699 A1 | 1/2006 | Olson et al. | | 2007/0175959 A1 | 8/2007 | Shelton, IV et al. |
| 2006/0016853 A1 | 1/2006 | Racenet | | 2007/0175960 A1 | 8/2007 | Shelton, IV et al. |
| 2006/0022014 A1 | 2/2006 | Shelton, IV et al. | | 2007/0175961 A1 | 8/2007 | Shelton, IV et al. |
| 2006/0022015 A1 | 2/2006 | Shelton, IV et al. | | 2007/0175962 A1 | 8/2007 | Shelton, IV et al. |
| 2006/0025809 A1 | 2/2006 | Shelton, IV | | 2007/0175964 A1 | 8/2007 | Shelton, IV et al. |
| 2006/0043147 A1 | 3/2006 | Mastri et al. | | 2007/0179528 A1 | 8/2007 | Soltz et al. |
| 2006/0049229 A1 | 3/2006 | Milliman et al. | | 2007/0187453 A1 | 8/2007 | Smith et al. |
| 2006/0049230 A1 | 3/2006 | Shelton, IV et al. | | 2007/0187454 A1 | 8/2007 | Scirica |
| 2006/0060630 A1 | 3/2006 | Shelton, IV et al. | | 2007/0187455 A1 | 8/2007 | Demmy et al. |
| 2006/0081678 A1 | 4/2006 | Ehrenfels et al. | | 2007/0194079 A1 | 8/2007 | Hueil et al. |
| 2006/0097026 A1 | 5/2006 | Shelton, IV | | 2007/0194080 A1 | 8/2007 | Swayze et al. |
| 2006/0124688 A1 | 6/2006 | Racenet et al. | | 2007/0194081 A1 | 8/2007 | Hueil et al. |
| 2006/0124689 A1 | 6/2006 | Arad et al. | | 2007/0194082 A1 | 8/2007 | Morgan et al. |
| 2006/0138193 A1 | 6/2006 | Viola et al. | | 2007/0213747 A1* | 9/2007 | Monassevitch et al. ...... 606/151 |
| 2006/0138194 A1 | 6/2006 | Viola et al. | | 2007/0221700 A1 | 9/2007 | Ortiz et al. |
| 2006/0151567 A1 | 7/2006 | Roy | | 2007/0221701 A1 | 9/2007 | Ortiz et al. |
| 2006/0151568 A1 | 7/2006 | Weller et al. | | 2007/0278277 A1 | 12/2007 | Wixey et al. |
| 2006/0151569 A1 | 7/2006 | Ehrenfels et al. | | 2007/0295780 A1 | 12/2007 | Shelton et al. |
| 2006/0175375 A1 | 8/2006 | Shelton, IV et al. | | 2008/0029570 A1 | 2/2008 | Shelton et al. |
| 2006/0180634 A1 | 8/2006 | Shelton, IV et al. | | 2008/0029571 A1 | 2/2008 | Shelton et al. |
| 2006/0201990 A1 | 9/2006 | Mastri et al. | | 2008/0029572 A1 | 2/2008 | Shelton et al. |
| 2006/0201991 A1 | 9/2006 | Mastri et al. | | 2008/0029573 A1 | 2/2008 | Shelton et al. |
| 2006/0226195 A1 | 10/2006 | Scirica et al. | | 2008/0029574 A1 | 2/2008 | Shelton et al. |
| 2006/0226196 A1 | 10/2006 | Hueil et al. | | 2008/0029575 A1 | 2/2008 | Shelton et al. |
| 2006/0255090 A1 | 11/2006 | Milliman et al. | | 2008/0029576 A1 | 2/2008 | Shelton et al. |
| 2006/0278680 A1 | 12/2006 | Viola et al. | | 2008/0029577 A1 | 2/2008 | Shelton et al. |
| 2006/0278681 A1 | 12/2006 | Viola et al. | | 2008/0048002 A1 | 2/2008 | Smith et al. |
| 2006/0289600 A1 | 12/2006 | Wales et al. | | 2008/0078800 A1 | 4/2008 | Hess et al. |
| 2006/0289602 A1 | 12/2006 | Wales et al. | | 2008/0078801 A1 | 4/2008 | Shelton et al. |
| 2007/0023477 A1 | 2/2007 | Whitman et al. | | 2008/0078802 A1 | 4/2008 | Hess et al. |
| 2007/0027469 A1 | 2/2007 | Smith et al. | | 2008/0078803 A1 | 4/2008 | Shelton et al. |
| 2007/0034669 A1 | 2/2007 | de la Torre et al. | | 2008/0078804 A1 | 4/2008 | Shelton et al. |
| 2007/0034670 A1 | 2/2007 | Racenet et al. | | 2008/0078805 A1 | 4/2008 | Omaits et al. |
| 2007/0045379 A1 | 3/2007 | Shelton, IV | | 2008/0078806 A1 | 4/2008 | Omaits et al. |

| Publication No. | Date | Inventor |
|---|---|---|
| 2008/0078807 A1 | 4/2008 | Hess et al. |
| 2008/0078808 A1 | 4/2008 | Hess et al. |
| 2008/0110958 A1 | 5/2008 | McKenna et al. |
| 2008/0110961 A1 | 5/2008 | Voegele et al. |
| 2008/0125812 A1 | 5/2008 | Zubik et al. |
| 2008/0132915 A1* | 6/2008 | Buckman et al. ............. 606/138 |
| 2008/0149685 A1 | 6/2008 | Smith et al. |
| 2008/0164296 A1 | 7/2008 | Shelton et al. |
| 2008/0169327 A1 | 7/2008 | Shelton et al. |
| 2008/0169328 A1 | 7/2008 | Shelton |
| 2008/0169329 A1 | 7/2008 | Shelton et al. |
| 2008/0169330 A1 | 7/2008 | Shelton et al. |
| 2008/0169331 A1 | 7/2008 | Shelton et al. |
| 2008/0169332 A1 | 7/2008 | Shelton et al. |
| 2008/0169333 A1 | 7/2008 | Shelton et al. |
| 2008/0210738 A1 | 9/2008 | Shelton et al. |
| 2008/0237296 A1 | 10/2008 | Boudreaux et al. |
| 2008/0237298 A1 | 10/2008 | Schall et al. |
| 2008/0277447 A1 | 11/2008 | Smith et al. |
| 2008/0283570 A1 | 11/2008 | Boyden et al. |
| 2008/0283571 A1 | 11/2008 | Boyden et al. |
| 2008/0283572 A1 | 11/2008 | Boyden et al. |
| 2008/0283574 A1 | 11/2008 | Boyden et al. |
| 2008/0283576 A1 | 11/2008 | Boyden et al. |
| 2008/0283577 A1 | 11/2008 | Boyden et al. |
| 2008/0287987 A1 | 11/2008 | Boyden et al. |
| 2008/0296343 A1 | 12/2008 | Schall et al. |
| 2008/0296344 A1 | 12/2008 | Cropper et al. |
| 2008/0296345 A1 | 12/2008 | Shelton, IV et al. |
| 2008/0296346 A1 | 12/2008 | Shelton, IV et al. |
| 2008/0296347 A1 | 12/2008 | Shelton, IV et al. |
| 2008/0302854 A1 | 12/2008 | Rethy et al. |
| 2008/0308601 A1 | 12/2008 | Timm et al. |
| 2008/0308602 A1 | 12/2008 | Timm et al. |
| 2008/0308603 A1 | 12/2008 | Shelton, IV et al. |
| 2008/0308604 A1 | 12/2008 | Timm et al. |
| 2008/0308606 A1 | 12/2008 | Timm et al. |
| 2008/0308607 A1 | 12/2008 | Timm et al. |
| 2008/0314954 A1 | 12/2008 | Boudreaux |
| 2008/0314955 A1 | 12/2008 | Boudreaux et al. |
| 2008/0314957 A1 | 12/2008 | Boudreaux |
| 2008/0314961 A1 | 12/2008 | Boudreaux et al. |
| 2008/0314962 A1 | 12/2008 | Boudreaux |
| 2009/0001121 A1 | 1/2009 | Hess et al. |
| 2009/0001123 A1 | 1/2009 | Morgan et al. |
| 2009/0001124 A1 | 1/2009 | Hess et al. |
| 2009/0001125 A1 | 1/2009 | Hess et al. |
| 2009/0001126 A1 | 1/2009 | Hess et al. |
| 2009/0001130 A1 | 1/2009 | Hess et al. |
| 2009/0005808 A1* | 1/2009 | Hess et al. ................ 606/219 |
| 2009/0008424 A1 | 1/2009 | Green |
| 2009/0039137 A1* | 2/2009 | Viola ..................... 227/176.1 |
| 2009/0050671 A1 | 2/2009 | Racenet et al. |
| 2009/0057370 A1 | 3/2009 | Marczyk et al. |
| 2009/0065549 A1 | 3/2009 | Viola |
| 2009/0065550 A1 | 3/2009 | Green et al. |
| 2009/0065551 A1 | 3/2009 | Green et al. |
| 2009/0078738 A1 | 3/2009 | Racenet et al. |
| 2009/0078739 A1 | 3/2009 | Viola |
| 2009/0084826 A1 | 4/2009 | Shah et al. |
| 2009/0090763 A1 | 4/2009 | Zemlok et al. |
| 2009/0090764 A1 | 4/2009 | Viola |
| 2009/0090765 A1 | 4/2009 | Blier et al. |
| 2009/0090766 A1 | 4/2009 | Knodel |
| 2009/0095790 A1 | 4/2009 | Whitman et al. |
| 2009/0101692 A1 | 4/2009 | Whitman et al. |
| 2009/0101694 A1 | 4/2009 | Marczyk |
| 2009/0105535 A1 | 4/2009 | Green |
| 2009/0108048 A1 | 4/2009 | Zemlok et al. |
| 2009/0108049 A1 | 4/2009 | Roy |
| 2009/0114699 A1 | 5/2009 | Viola |
| 2009/0114700 A1 | 5/2009 | Marczyk |
| 2009/0114701 A1 | 5/2009 | Zemlok et al. |
| 2009/0209946 A1 | 8/2009 | Swayze et al. |
| 2009/0209990 A1 | 8/2009 | Yates et al. |
| 2009/0218384 A1 | 9/2009 | Aranyi |
| 2009/0236393 A1 | 9/2009 | Viola |
| 2009/0236395 A1 | 9/2009 | Scirica |
| 2009/0242610 A1 | 10/2009 | Shelton, IV et al. |
| 2009/0242611 A1 | 10/2009 | Hathaway et al. |
| 2009/0255974 A1 | 10/2009 | Viola |
| 2009/0255975 A1 | 10/2009 | Zemlok et al. |
| 2009/0255976 A1 | 10/2009 | Marczyk et al. |
| 2009/0255977 A1 | 10/2009 | Zemlok |
| 2009/0261142 A1 | 10/2009 | Milliman et al. |
| 2009/0261144 A1 | 10/2009 | Sniffin et al. |
| 2009/0261145 A1 | 10/2009 | Heinrich et al. |
| 2009/0266868 A1 | 10/2009 | Wenchell et al. |
| 2009/0272784 A1 | 11/2009 | Farascioni |
| 2009/0272787 A1 | 11/2009 | Scirica |
| 2009/0277946 A1 | 11/2009 | Marczyk |
| 2009/0277947 A1 | 11/2009 | Viola |
| 2009/0277949 A1* | 11/2009 | Viola et al. ................. 227/178.1 |
| 2009/0283568 A1 | 11/2009 | Racenet et al. |
| 2009/0289096 A1 | 11/2009 | Shelton, IV et al. |
| 2009/0302090 A1 | 12/2009 | Shah |
| 2009/0302091 A1 | 12/2009 | Shah |
| 2009/0306708 A1 | 12/2009 | Shah |
| 2009/0308907 A1 | 12/2009 | Nalagatla et al. |
| 2009/0308908 A1 | 12/2009 | Green et al. |
| 2009/0308909 A1 | 12/2009 | Nalagatla et al. |
| 2009/0314820 A1 | 12/2009 | Green et al. |
| 2009/0314821 A1 | 12/2009 | Racenet |
| 2010/0001036 A1 | 1/2010 | Marczyk et al. |
| 2010/0006620 A1 | 1/2010 | Sorrentino et al. |
| 2010/0012702 A1 | 1/2010 | Marczyk |
| 2010/0012703 A1 | 1/2010 | Calabrese et al. |
| 2010/0012704 A1 | 1/2010 | Racenet et al. |
| 2010/0025452 A1 | 2/2010 | Whitman |
| 2010/0032470 A1 | 2/2010 | Hess et al. |
| 2010/0044411 A1 | 2/2010 | Viola |
| 2010/0065605 A1 | 3/2010 | Shelton, VI et al. |
| 2010/0065606 A1 | 3/2010 | Stopek et al. |
| 2010/0065608 A1 | 3/2010 | Olson et al. |
| 2010/0069942 A1 | 3/2010 | Shelton, IV et al. |
| 2010/0072251 A1 | 3/2010 | Baxter, III et al. |
| 2010/0072252 A1 | 3/2010 | Baxter, III et al. |
| 2010/0072253 A1 | 3/2010 | Baxter, III et al. |
| 2010/0072254 A1 | 3/2010 | Aranyi et al. |
| 2010/0072255 A1 | 3/2010 | Olson et al. |
| 2010/0072256 A1 | 3/2010 | Baxter, III et al. |
| 2010/0072258 A1 | 3/2010 | Farascioni |
| 2010/0076429 A1 | 3/2010 | Heinrich |
| 2010/0076459 A1 | 3/2010 | Farascioni |
| 2010/0116867 A1* | 5/2010 | Balbierz et al. ............. 227/175.1 |
| 2011/0192881 A1* | 8/2011 | Balbierz et al. ............. 227/176.1 |

FOREIGN PATENT DOCUMENTS

| | | |
|---|---|---|
| DE | 2744824 | 4/1978 |
| DE | 2903159 | 1/1980 |
| DE | 3114135 | 10/1982 |
| DE | 4213426 | 10/1992 |
| DE | 4300307 | 7/1994 |
| EP | 0041022 | 12/1981 |
| EP | 0136950 | 4/1985 |
| EP | 0140552 | 5/1985 |
| EP | 0156774 | 10/1985 |
| EP | 0216532 | 4/1987 |
| EP | 0220029 | 4/1987 |
| EP | 0213817 | 11/1987 |
| EP | 0273468 | 7/1988 |
| EP | 0324166 | 7/1989 |
| EP | 0324635 | 7/1989 |
| EP | 0324637 | 7/1989 |
| EP | 0324638 | 7/1989 |
| EP | 0369324 | 5/1990 |
| EP | 0373762 | 6/1990 |
| EP | 0380025 | 8/1990 |
| EP | 0399701 | 11/1990 |
| EP | 0449394 | 10/1991 |
| EP | 0484677 | 5/1992 |
| EP | 0489436 | 6/1992 |
| EP | 0503662 | 9/1992 |
| EP | 0514139 | 11/1992 |
| EP | 0536903 | 4/1993 |
| EP | 0537572 | 4/1993 |
| EP | 0539762 | 5/1993 |
| EP | 0545029 | 6/1993 |

| | | | | | | |
|---|---|---|---|---|---|---|
| EP | 0552050 | 7/1993 | | GB | 1352554 | 4/1971 |
| EP | 0552423 | 7/1993 | | GB | 1452185 | 10/1976 |
| EP | 0579038 | 1/1994 | | GB | 1555455 | 11/1979 |
| EP | 0589306 | 3/1994 | | GB | 2048685 | 12/1980 |
| EP | 0591946 | 4/1994 | | GB | 2070499 | 9/1981 |
| EP | 0592243 | 4/1994 | | GB | 2141066 | 12/1984 |
| EP | 0593920 | 4/1994 | | GB | 2165559 | 4/1986 |
| EP | 0598202 | 5/1994 | | SU | 659146 | 4/1979 |
| EP | 0598579 | 5/1994 | | SU | 728848 | 5/1980 |
| EP | 0621006 | 10/1994 | | SU | 980703 | 1/1983 |
| EP | 0621009 | 10/1994 | | SU | 990220 | 1/1983 |
| EP | 0656188 | 6/1995 | | WO | WO 89/10094 | 11/1989 |
| EP | 0365153 | 8/1995 | | WO | WO9210976 | 7/1992 |
| EP | 0666057 | 8/1995 | | WO | WO 9308754 | 5/1993 |
| EP | 0705571 | 4/1996 | | WO | WO8302247 | 7/1993 |
| EP | 0760230 | 3/1997 | | WO | WO 9314706 | 8/1993 |
| FR | 2542188 | 9/1984 | | | | |
| FR | 2660851 | 10/1991 | | * cited by examiner | | |
| FR | 2681775 | 10/1991 | | | | |

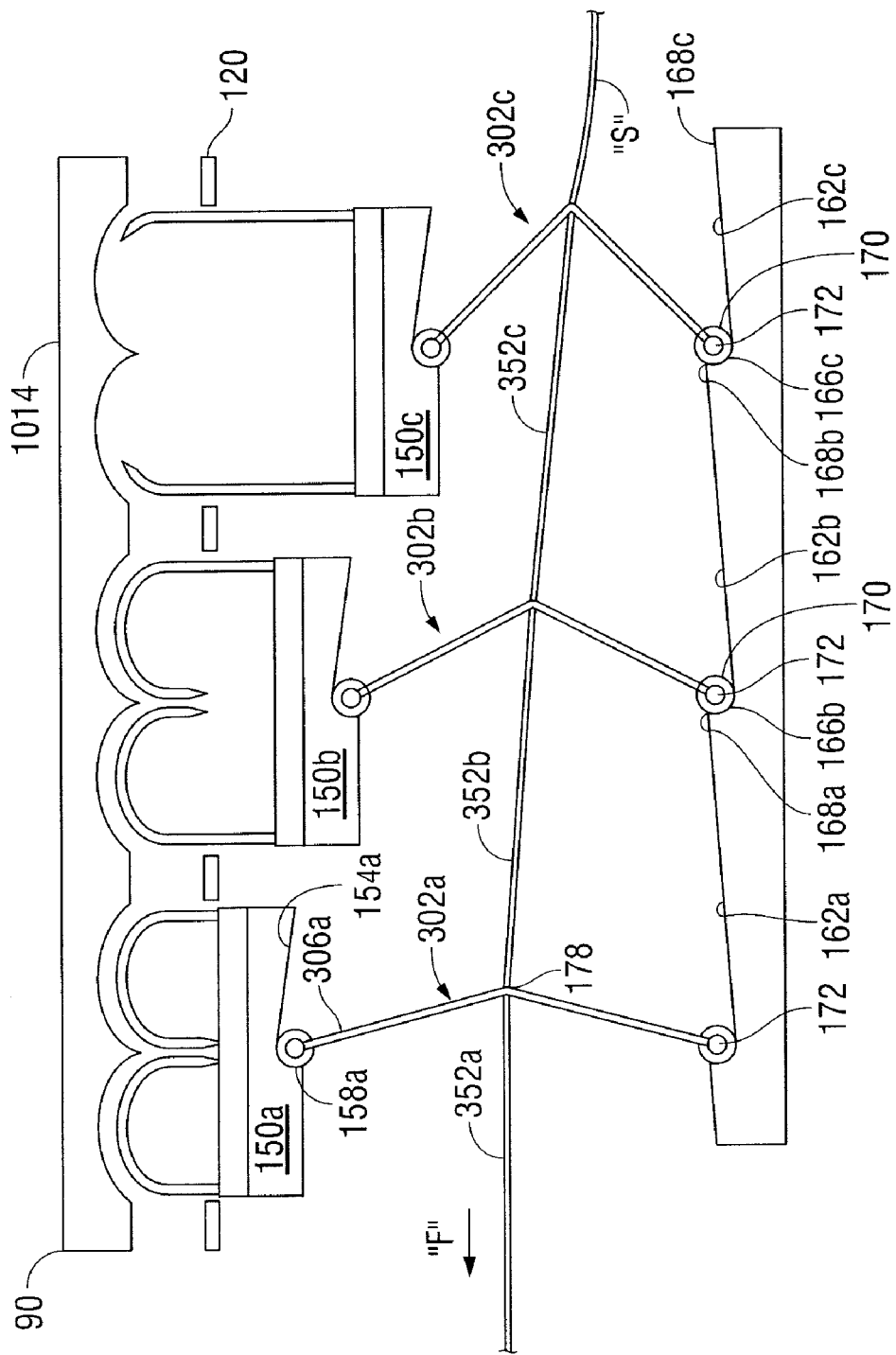

SURGICAL FASTENER APPLYING APPARATUS

BACKGROUND

1. Technical Field

The present disclosure relates to surgical fastener applying apparatus and more particularly to surgical fastener apparatus that employs a fastener forming mechanism that includes a linkage system for sequentially applying a plurality of surgical fasteners to body tissue.

2. Background of the Related Art

Commercially available surgical fastener applying apparatuses wherein tissue is first grasped or clamped between opposing jaw structures and then joined by means of surgical fasteners are well known in the art. The fasteners are typically in the form of surgical staples however, other surgical fasteners may also be utilized, for example, clips or two part polymeric surgical fasteners.

To form the surgical fasteners, manufacturers typically employ an actuation mechanism that includes or is in operative communication with a wedge shaped sled that moves axially towards a distal end of a loading unit associated with the surgical fastener applying apparatus. The loading unit may be a disposable loading unit (DLU) or a single use loading unit (SULU). Additionally, the loading unit may be of the straight or curved type. Typically, the sled engages a corresponding pusher that moves orthogonally relative to an axis defined by the loading unit of. The pushers are configured to drive a corresponding staple through tissue and against a receiving pocket of an anvil associated with the surgical fastener applying apparatus to form the staple and close tissue. In this instance, the staples are fired sequentially, thus, minimizing the firing force and the size of a distal end of the surgical fastener applying apparatus. Accordingly, surgical fastener applying apparatuses of this type are well suited for use in laparoscopic procedures.

Costs associated with the manufacturing process of the above-referenced actuation mechanism and sleds associated therewith are relatively high due to design constraints associated with the sled and/or a driving mechanism employed to move the sled. Additionally, because the size of the loading unit is proportionate to the size of the sled and/or driving mechanism, the loading unit is typically larger than would be desired. Accordingly, it may prove useful to minimize the size of the loading unit while maximizing a mechanical advantage at the end of forming a staple.

SUMMARY

The present disclosure relates a surgical fastener cartridge. The surgical fastener cartridge includes a cartridge body including a tissue contacting surface. The tissue contacting surface includes a plurality of fastener retention slots. A plurality of surgical fasteners is operatively disposed in the plurality of fastener retention slots. An actuation mechanism is housed within the cartridge body. The actuation mechanism includes a plurality of pushers operably associated with the plurality of surgical fasteners. Each pusher may be configured for ejecting an associated surgical fastener towards a depression in an anvil. The actuation mechanism includes an internal channel housing defined by and operably disposed within the cartridge body. The actuation mechanism includes a plurality of pivotably connected link assemblies. Each link assembly is releasably engaged with a corresponding bottom surface associated with each the pushers and a corresponding top surface associated with the internal channel housing.

Each link assembly is operably coupled to one another via an activation structure for transitioning each of the link assemblies, wherein the plurality of pivotably connected link assemblies are transitionable from an initial position where each of the link assemblies are engaged with the corresponding bottom surface associated with each of the pushers and the corresponding top surface associated with the internal channel housing. Each of the link assemblies is transitionable through a subsequent position where each of the link assemblies is configured to cause the corresponding pusher to contact and, subsequently, eject the associated surgical fastener towards the depression in the anvil, and to a final position where each of the link assemblies are disengaged from the bottom and top surfaces of the pusher and internal channel housing, respectively.

In embodiments, the activation structure may be adapted to operatively connect to a drive assembly associated with a surgical fastening apparatus.

In embodiments, the tissue contacting surface may include a knife slot configured to accommodate longitudinal movement of a cutting element.

In embodiments, each of the pushers and corresponding top surface associated with the internal channel housing may include a generally arcuate portion configured to releasable engage respective proximal ends of the first and second link members.

In embodiments, the generally arcuate portion associated with each of the pushers may be disposed near the center of the pushers and is in vertical registration with a corresponding generally arcuate portion of the top surface of the internal housing.

In embodiments, the activation structure may be configured to move the each of the link assemblies when the activation structure is pulled proximally.

In embodiments, the activation structure for transitioning each of the link assemblies may include a cable including a plurality of cable segments between each of the link assemblies, wherein each cable segment includes a amount of slack.

In embodiments, each of the cable segments of the cable is operably coupled to a corresponding distal end of the first and second links.

In embodiments, the amount of slack of each cable segment increases from a proximal most cable segment to a distal most cable segment, the amount of slack configured to facilitate sequential ejection of the surgical fasteners.

In embodiments, each of the link assemblies includes at least two link members including a first link having a proximal end releasably engaged with a corresponding bottom surface associated with each of the pushers and a second link having a proximal end releasably engaged with a corresponding top surface associated with the internal channel housing. Each of the first and second links including distal ends pivotably coupled to each other.

In embodiments, each of the first and second links of the link assemblies may be disposed in a generally oblique relation relative to each other.

In an alternative embodiment, the actuation mechanism includes a plurality of pivotably connected link members. Each of the plurality of link members is operably engaged with a corresponding bottom surface associated with each the pushers and the internal channel housing. A drive rod is configured for longitudinal movement within the cartridge body and configured to sequentially contact at least a portion of each of the link members when the drive rod is moved distally through the cartridge body such that the link members cause the corresponding pusher to contact and, subsequently, eject the associated surgical fastener towards the depression in the anvil.

In embodiments, the at least a portion of each of the link members that contacts the drive rod is a lower portion of the proximal end of the first link.

In embodiments, the lower portion of the proximal end of the first link member extends in a generally orthogonal relation with respect to the longitudinal axis defined through the cartridge body.

In embodiments, the first and second link members are offset from each other.

In embodiments, each of the link members may be configured such that during distal translation of the drive rod through the cartridge body, each of the lower portions of the link members is caused to move from an initial position wherein the lower portion of the link member is distal relative to a distal end of the drive rod and inside the path of translation of the drive rod to a final position wherein the lower portion of the first link member is proximal relative to a distal end of the drive rod and outside the path of translation of the drive rod.

In embodiments, the drive rod may be configured to slide under the lower portion of the first link member when the lower portion is in the final position.

In embodiments, the drive rod may be flexible and/or elastic.

BRIEF DESCRIPTION OF THE DRAWINGS

Various embodiments of the present disclosure are described hereinbelow with references to the drawings, wherein:

FIGS. 4A-4D are enlarged partial side views of a surgical fastener cartridge shown in FIG. 1 with the actuation mechanism shown in various positions during operation;

DETAILED DESCRIPTION OF THE EMBODIMENTS

Figure 1:
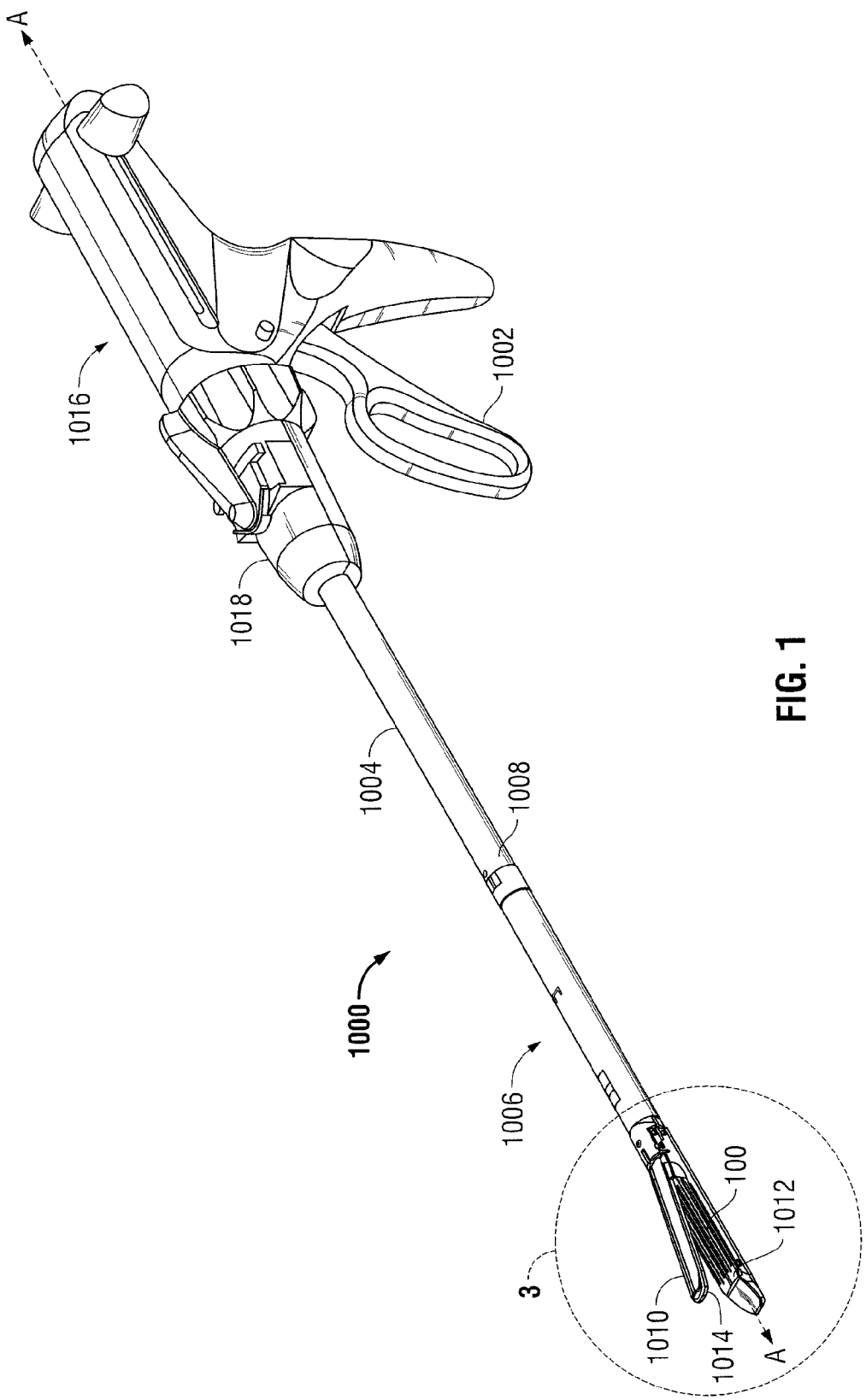
FIG. 1 is a perspective view of a surgical fastener applying apparatus including a linear loading unit that employs an actuation mechanism in accordance with an embodiment of the present disclosure.

Various exemplary embodiments of the presently disclosed surgical fastener cartridge will now be described in detail with reference to the drawings wherein like references numerals identify similar or identical elements. In the drawings and in the description which follows, the term "proximal" will refer to the end of the component that is closer to the operator during use, while the term "distal" will refer to the end of the component that is further from the operator, as is traditional and conventional in the art. In addition, the term "surgical fastener" should be understood to include any structure formed of a biocompatible material that is suitable for the intended purpose of joining tissue together, including but not being limited to surgical staples, clips, and the like.

Figure 3:
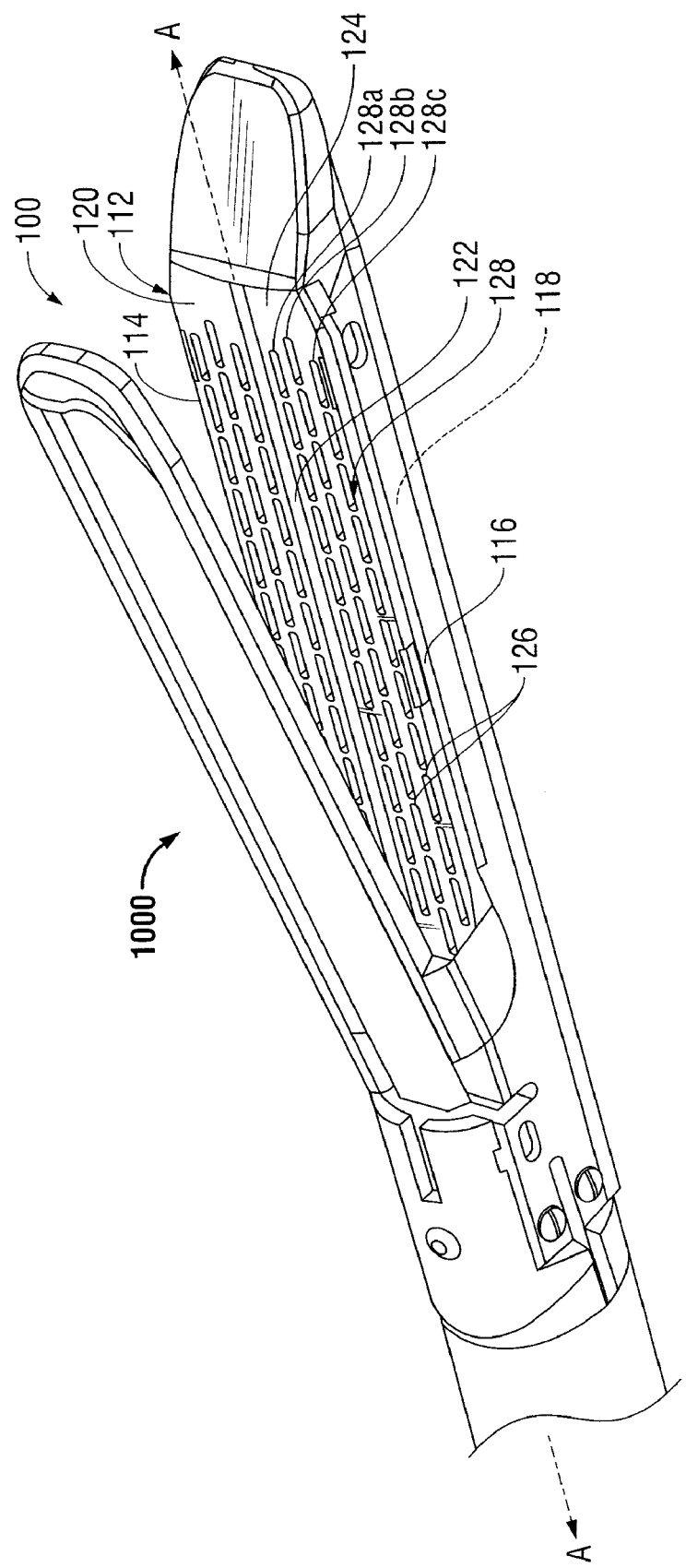
FIG. 3 is an enlarged view of detail area 3 of FIG. 1.

With reference to FIG. 1, a linear surgical fastener applying apparatus 1000 that employs a surgical fastener cartridge 100 is illustrated. Surgical fastener applying apparatus 1000 is used to sequentially apply a plurality of surgical fasteners to a patient's tissue. Surgical fastener apparatus 1000 may be configured for use, subsequent sterilization and reuse, or may be configured for single use. Surgical fastener applying apparatus 1000 includes a housing 1016 that includes a barrel portion 1018, a movable handle 1002, an elongated shaft 1004 (defining a longitudinal axis "A-A") extending distally therefrom, and an operative tool 1006 coupled to a distal end 1008 of the elongated shaft 1004. In general, operative tool 1006 is adapted to clamp, sequentially fasten together, and sever adjacent tissue segments along a cut-line. Operative tool 1006 includes a pair of opposed jaws 1010, 1012 pivotally coupled with respect to one another and respectively including an anvil member 1014 and cartridge 100 that are approximated relative to one another during use. The anvil includes an anvil plate 90 having surgical fastener forming depressions 91 (FIG. 4A) that are aligned with, and/or are in vertical registration with slots 126 defined in the cartridge 100 (FIG. 3). The fasteners 130 emerge through the slots 126, to be driven against anvil plate 90, as seen in FIG. 4B, for example. For a more detailed discussion of the approximation and firing of surgical fastener applying apparatus 1000, reference is made to commonly owned U.S. Pat. Nos. 7,258,262 and 5,865,361 currently assigned to Tyco Healthcare Group LP, the entire contents of which are incorporated herein by reference. The operative tool 1006 may comprise a removable and replaceable loading unit for the apparatus 1000.

Figure 2:
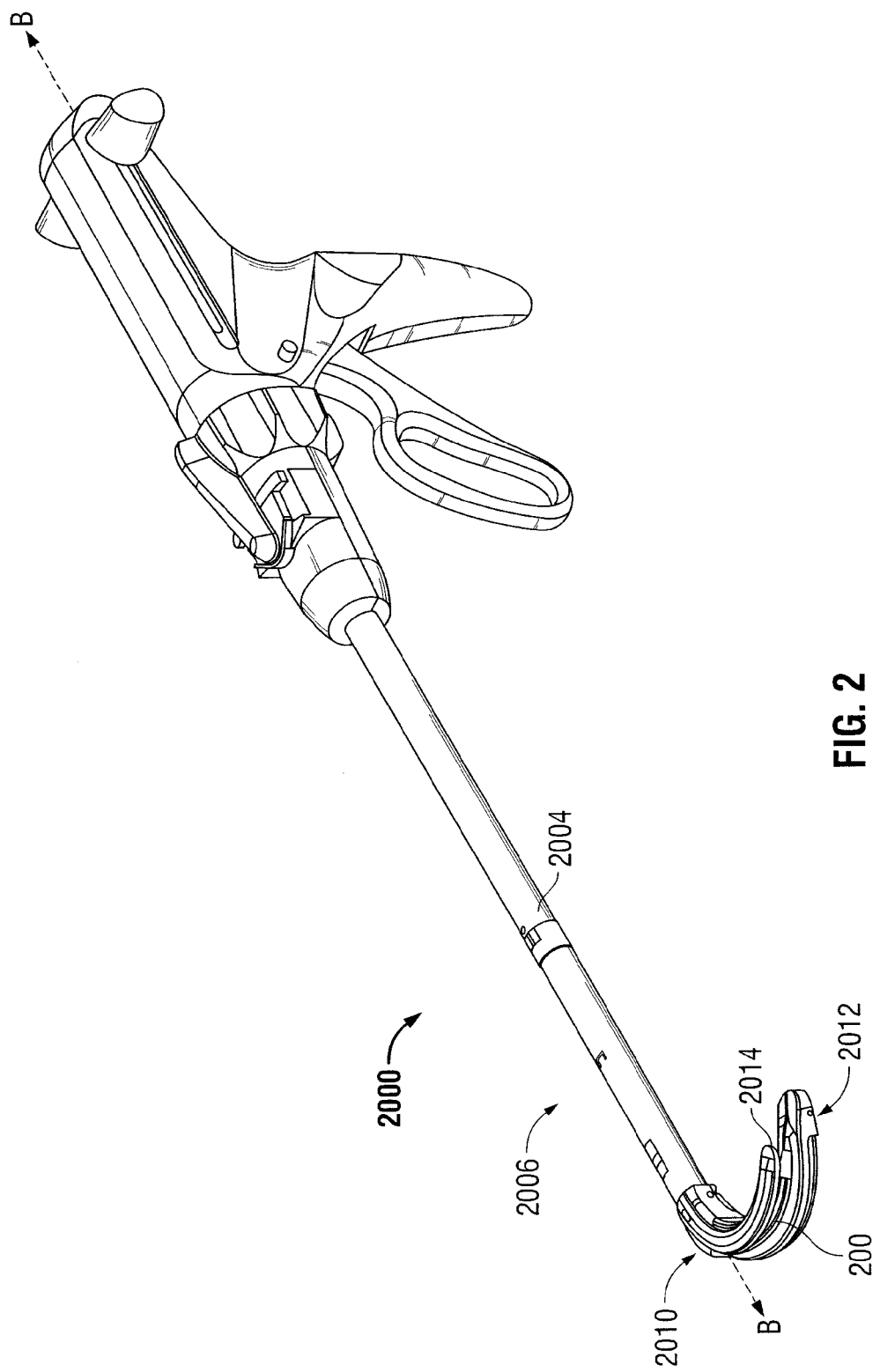
FIG. 2 is a perspective view of the surgical fastener applying apparatus depicted in FIG. 1 including a curved loading unit that employs an actuation mechanism in accordance with an alternate embodiment of the present disclosure.

With reference to FIG. 2, surgical fastener applying apparatus 2000 is shown operably coupled to an operative tool 2006 configured for use with a surgical fastener cartridge 200. A distinguishing feature of the operative tool 2006 when compared to operative tool 1006 is its curved jaw members including an anvil and cartridge associated therewith. That is, operative tool 2006 includes a pair of opposed jaws 2010, 2012 that are each curved with respect to a longitudinal axis B-B, defined by elongated shaft 2004. As with the jaw members 1010, 1012 of operative tool 1006, jaws 2010, 2012 are pivotally coupled with respect to one another and respectively including an anvil member 2014 and cartridge 200 that are approximated relative to one another during use. The curved jaw members 2010, 2012 facilitate performing certain types of surgical procedures. For example, curved jaw members 2010, 2012, as compared to linear jaw members (such as the jaw members 1010. 1020 illustrated in FIG. 1), may help facilitate access to lower pelvis regions, e.g., during lower anterior resection ("LAR"). Additionally, the inclusion of curved jaw members 2010, 2012 may allow increased visualization to a surgical site and may also allow more room for a surgeon to manipulate target tissue or the jaw members 2010, 2012 themselves with his or her hand.

The structural and functional features of the cartridges 100 and 200 are substantially equivalent. Thus, for the purposes of brevity, and so as not to obscure the present disclosure with redundant information, the structural and functional features of cartridges 100 and 200 will be described hereinafter with reference to cartridge 100. Cartridge 100 will be described in terms of use with the surgical fastener applying apparatus 1000 and the operative tool 1006 of FIG. 1. Unless otherwise noted, it is assumed that the description that follows herein applies equally to the cartridge 200 and operative tool 2006. The features unique to cartridge 200 and operative tool 2006 will be described hereinafter only to the extent necessary to facilitate understanding of the present disclosure.

Figure 4A:
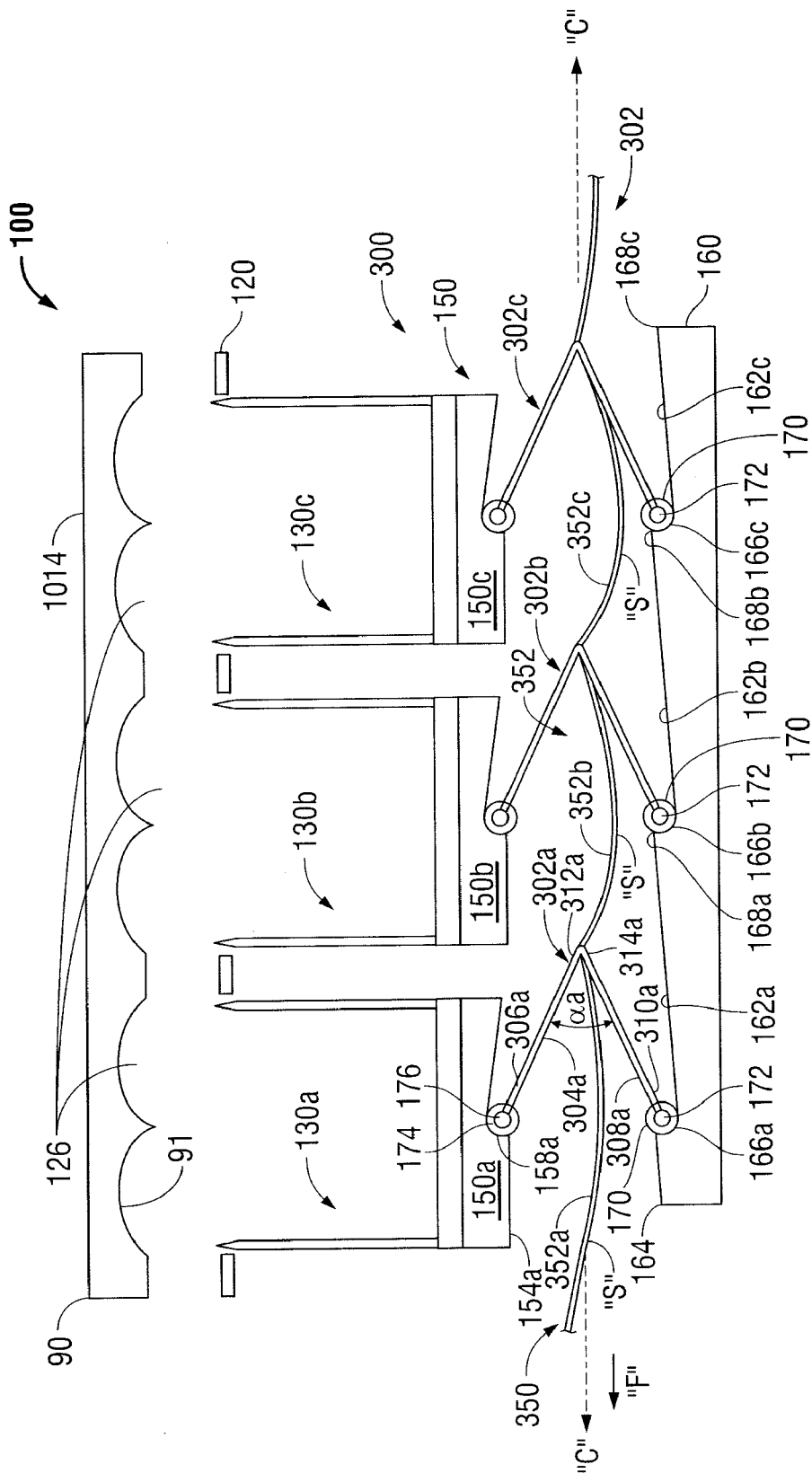
Figure 4B:
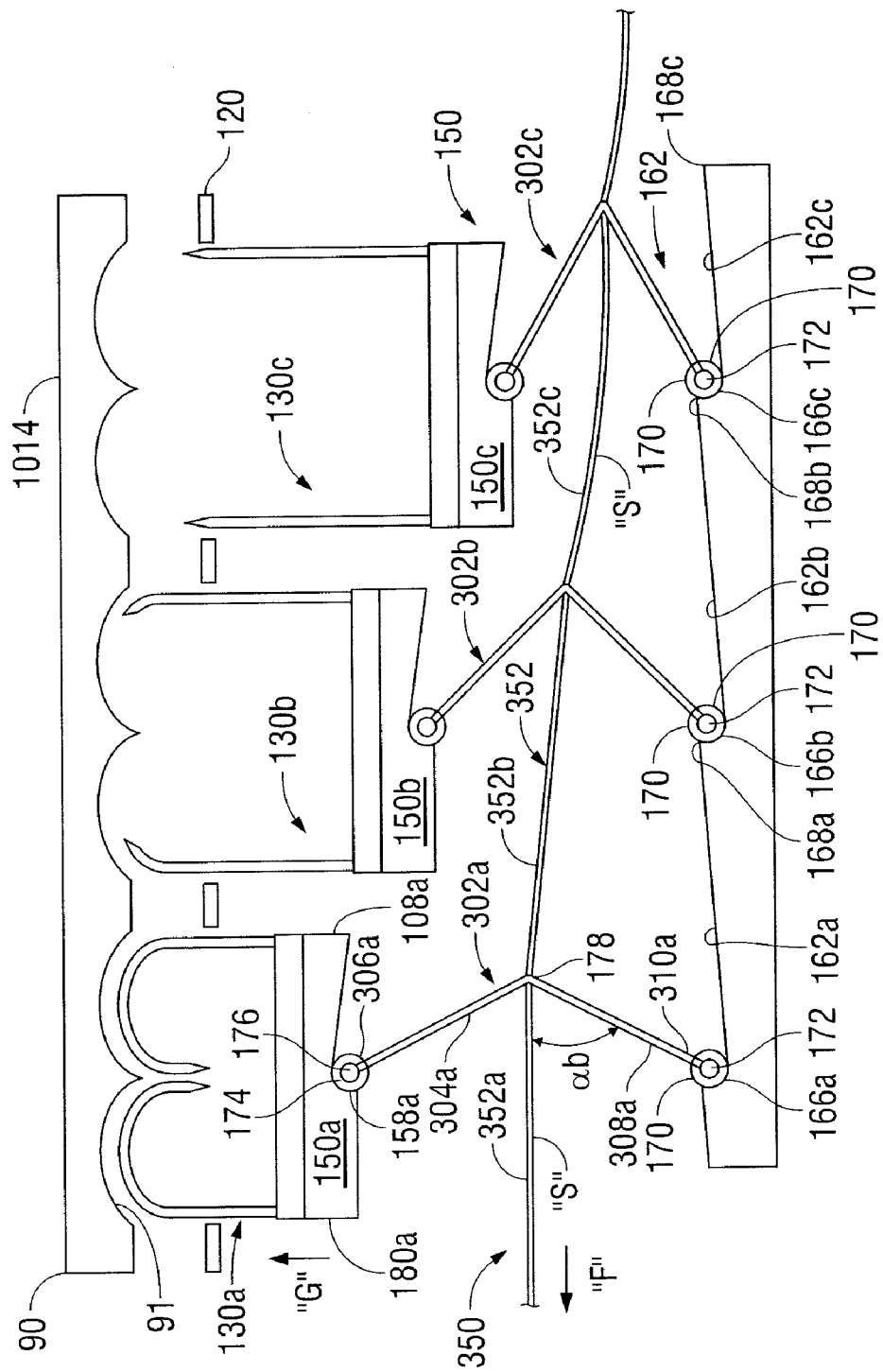
Figure 4D:
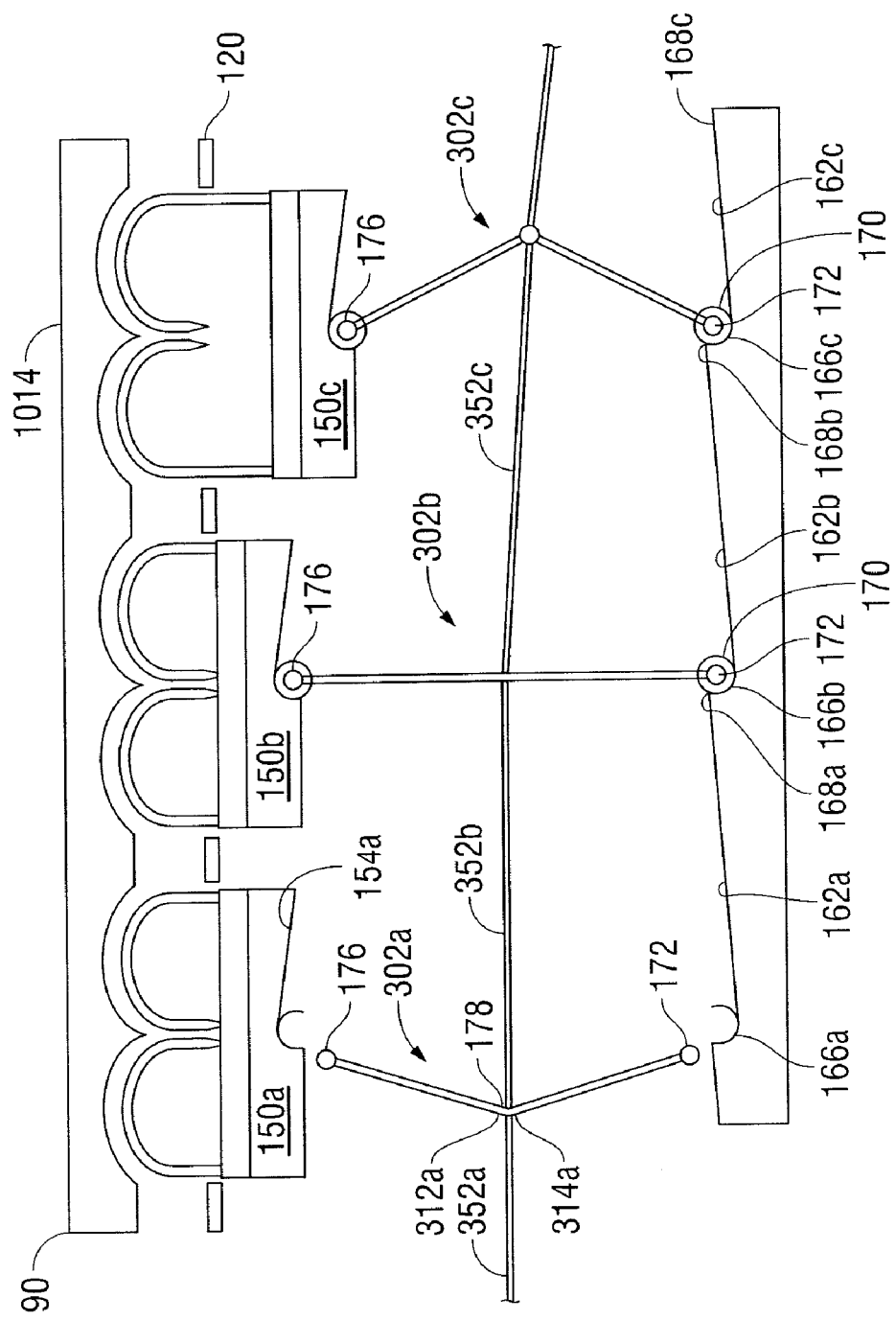

With reference to FIG. 3-4D, and initially with reference to FIG. 3, cartridge 100 is shown. Cartridge 100 extends along the longitudinal axis "A-A" and includes a cartridge body 112 with a pair of opposed side walls 114, 116, a bottom wall 118, and a tissue contacting surface 120. The tissue contacting surface 120 includes a channel 122 that is configured to accommodate longitudinal movement of a knife (not shown), or other suitable cutting element, such that stapled tissue may be severed along a cut-line. The cartridge also defines longitudinally extending recesses that accommodate part of the surgical fastener forming mechanism and are discussed below. The tissue contacting surface 120 includes a plurality of fastener retention slots 126 that extend from the tissue contacting surface 120 into the cartridge and intersect with the longitudinally extending recesses. The fastener retention slots 126 are arranged in a plurality of rows 128 that extend substantially the length of the cartridge 100. As shown in FIG. 3, the fastener retention slots 126 are arranged into a pair of first (inner) rows $128_A$ that are spaced laterally from the channel 122 and on opposite sides thereof, a pair of second (middle) rows $128_B$ that are spaced laterally from the pair of first rows $128_A$ and on opposite sides of the channel 122, and a pair of third (outer) rows $128_C$ that are spaced laterally from the pair of second rows $128_B$ and on opposite sides of channel 122. While the cartridge 100 is depicted as including pairs of first, second, and third rows $128_A$, $128_B$, $128_C$, respectively, it is within the purview of the present disclosure to have more or fewer rows of the fastener retention slots 126 disposed on cartridge 100. Each of the fastener retention slots 126 is configured to receive one of a plurality of surgical fasteners 130 and pushers 150 therein such that the surgical fasteners 130 are deployed in rows (e.g., inner, middle, and outer rows) on opposite sides of the cut-line created in the tissue during fastening. In embodiments, pushers 150 are at least partially disposed in the fastener retention slots 126.

Cartridge 200 (FIG. 2) includes substantially the same components as described above with respect to cartridge 100. A distinguishing feature between the cartridges 200 and 100 is that the cartridge 200 does not extend along the longitudinal axis "B-B" and, as a result thereof, the placement of above-referenced components within the cartridge 200 will be offset from the longitudinal axis "B-B."

Figure 5:
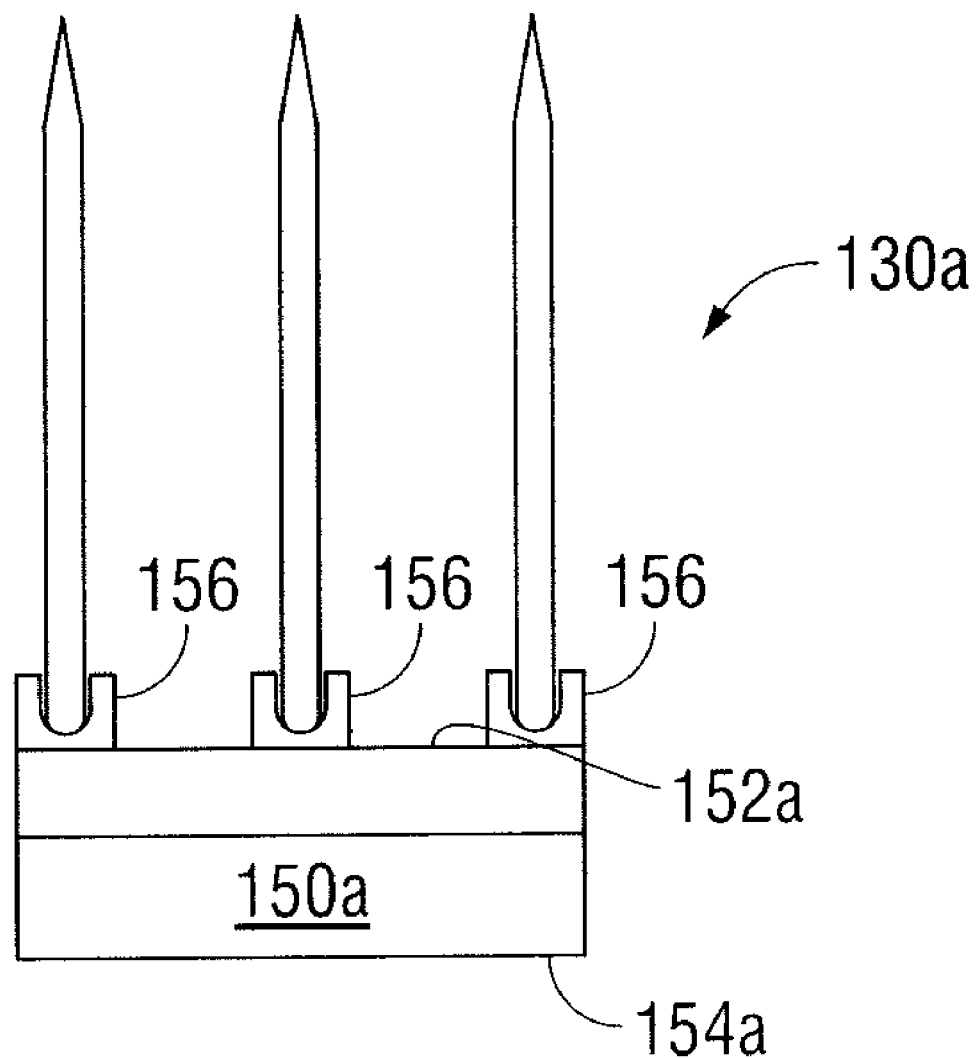
FIG. 5 illustrates a pusher and surgical fastener set associated with the actuation mechanism of FIGS. 4A-4D.

With reference to now to FIG. 4A, cartridge 100 includes an actuation mechanism 300. The actuation mechanism 300 of the present disclosure may be employed with both cartridges 100 or 200 and straight or curved operable tools 1006 and 2006, respectively. The actuation mechanism 300 is configured to sequentially eject a plurality of surgical fasteners 130 from the first, second, and third rows $128_A$, $128_B$, $128_C$, respectively. With this purpose in mind, actuation mechanism 300 includes a plurality of pushers 150, a corresponding plurality of pivotably connected linkages or link assemblies 302 and an activation structure 350 for transitioning each of the link assemblies. More particularly, each of the pushers 150 and corresponding link assembly 302 is configured to eject a "set" of surgical fasteners 130 (see FIG. 5, with respect to a set of surgical fastener $130_a$, for example), wherein a set of surgical fasteners 130 is defined as three adjacent surgical fasteners 130 extending laterally across the first, second, and third rows $128_A$, $128_B$, $128_C$, respectively, to be described in more detail below.

Actuation mechanism 300 is operably housed within the cartridge body 112 and is configured to sequentially eject the plurality surgical fasteners 130 from the cartridge body 112 on opposite sides of the channel 122 and toward the anvil 90. To this end, an internal channel housing 160 is defined by and operably disposed within the cartridge body 112 on opposite sides of the channel 122. Channel housing 160 is operably disposed adjacent and grounded to a bottom portion of the cartridge body 112 and is in operative alignment with each of the first, second, and third rows $128_A$, $128_B$, $128_C$, respectively, of the cartridge 100 for ejecting a corresponding set of surgical fasteners 130. In the embodiment illustrated in FIGS. 4A-4D, the channel housing 160 extends along a length of the cartridge body 112 and includes a top surface 164 having a plurality of recesses or engagement surfaces 162 (see FIG. 4B, for example) that are disposed at predetermined locations along the top surface 164 of channel housing 160. The plurality of engagement surfaces 162 includes engagement surfaces $162_a$, $162_b$, and $162_c$. Each of the engagement surfaces $162_a$, $162_b$, and $162_c$ includes a respective corresponding proximal end $166_a$, $166_b$, and $166_c$ having a generally arcuate configuration. This arcuate configuration facilitates pivotable movement of a corresponding link assembly 302 when the actuation mechanism 300 is activated. Each of the engagement surfaces $162_a$, $162_b$, and $162_c$ includes a corresponding distal end $168_a$, $168_b$, and $168_c$ that form part of a proximal end of an adjacent engagement surface. More particularly, a distal end $168_a$ forms part of proximal end $166_b$, a distal end $168_b$ forms part of proximal end $166_c$, and so on (see FIG. 4A, for example). In the embodiment illustrated in FIGS. 4A-4D, each of the engagement surfaces $162_a$, $162_b$, and $162_c$ is angled or slanted relative to the axis "A" Alternatively, each of the engagement surfaces $162_a$, $162_b$, and $162_c$ may be parallel to the axis "A", i.e., not slanted. Each of the engagement surfaces $162_a$, $162_b$, and $162_c$ includes a respective break-away bridge 170 that is configured to pivotably and releasably retain a portion of a corresponding link assembly 302. More particularly, break-away bridge 170 operably couples to a pivot pin 172 that pivotably connects to a corresponding link assembly 302. In embodiments, each of the break-away bridges 170 may be monolithically formed with the top surface 164 of the channel housing 160 or a separate component attached by suitable means. In either instance, the break-away bridge 170 separates or otherwise releases the corresponding link assembly 302 from the top surface 164 of the channel housing 160, to be described in greater detail below.

With continued reference to FIG. 4A, actuation mechanism 300 includes a plurality of pushers 150 that are operably aligned with the plurality of engagement surfaces 162. So as not to obscure the present disclosure with redundant information, the actuation mechanism 300 is described in terms of use with three (3) pushers 150. In the embodiment illustrated in FIGS. 4A-4D, pushers 150 include pushers $150_a$, $150_b$ and $150_c$. As noted above, pushers 150 are operably associated with a corresponding set of the surgical fasteners 130. More particularly, a pusher $150_a$ is operably associated with a set of surgical fasteners $130_b$, a pusher $150_b$ is operably associated with a set of surgical fasteners $130_b$, and a pusher $150_c$ is operably associated with a set of surgical fasteners $130_c$. For the purposes of brevity, and unless otherwise noted, the operative features of pushers 150 and corresponding sets of surgical fasteners 130 is described hereinafter with reference to a pusher 150, and corresponding set of surgical fasteners $130_a$.

Pusher $150_a$ is configured to eject the corresponding set of surgical fasteners $130_a$ towards a depression, e.g., a depression 91, in an anvil. With this purpose in mind, a pusher $150_a$ includes a surgical fastener contacting top surface 152, (see FIG. 5, for example) in vertical registration with the set of surgical fasteners $130_a$. Top surface $152_a$ is dimensioned to contact each of the surgical fasteners 130 in the set of surgical fasteners $130_a$. Thus, when pusher 150, is caused to move upward and contact a corresponding set of surgical fasteners $130_a$, a surgical fastener 130 in the set of surgical fasteners 130, is ejected through a respective first, second, and third rows $128_A$, $128_B$, $128_C$. Top surface $152_a$ includes a generally flat configuration that allows the surgical fasteners 130 in the set of surgical fasteners $130_a$ to form a staple line that is uniform, i.e., a hemostatic effect associated with each of the formed surgical fasteners 130 is uniform across the staple line. Alternatively, an embodiment of the present disclosure may include a top surface $152_a$ may include one or more protuberances or grooves 156 (FIG. 5) configured to vary a height of the top surface $152_a$ such that the surgical fasteners 130 in the set of surgical fasteners $130_a$ form a staple line that is non-uniform, i.e., a hemostatic effect associated with each of the formed surgical fasteners 130 is non-uniform across the staple line. For example, in the alternative embodiment, a surgical fastener formed closer to the channel 122 provides a greater hemostatic effect to stapled tissue than a surgical fastener formed further from the channel 122. For a more detailed description of varying surgical fastener and/or pusher configurations to achieve a desired hemostatic effect, reference is made to commonly-owned U.S. patent application Ser. Nos. 12/410,850 and 12/427,794, the entire contents of each hereby incorporated by reference. Pusher $150_a$ includes a bottom engagement surface 154, (see FIGS. 4C and 4D). Engagement surface $154_a$ includes a proximal end 180, (see FIG. 4B), a median end 158, having a generally arcuate configuration (FIG. 4A), and a distal end 108a. As with the proximal end $166_a$ of engagement surface 162, of channel housing 160, this arcuate configuration facilitates pivotable movement of a corresponding link assembly 302 when the actuation mechanism 300 is activated. In the embodiment illustrated in FIGS. 4A-4D, engagement surface $154_a$ is slanted relative to the axis "A". Alternatively, the engagement surface 154, may be parallel to the axis "A", i.e., not slanted. Engagement surface $154_a$ includes a respective break-away bridge 174 configured to pivotably and releasably retain a portion of a corresponding link assembly 302. More particularly, break-away bridge 174 operably couples to a pivot pin 176 that pivotably connects to a corresponding link assembly 302. In embodiments, each of the break-away bridges 174 may be monolithically formed with engagement surface 154, of pusher $150_a$ or a separate component attached by suitable means. In either instance, the break-away bridge 174 separates or otherwise releases the corresponding link assembly 302 from the engagement surface $154_a$ of pusher $150_a$, to be described in greater detail below.

The actuation mechanism 300 includes a linkage system in the form of a plurality of pivotably connected link assemblies 302. Each of the link assemblies 302 engages a corresponding bottom surface associated with each of the pushers (e.g., engagement surface $154_a$) and corresponding engagement surface associated with the internal channel housing (e.g., engagement surface $162_a$). Each of the link assemblies 302 causes a corresponding pusher (e.g., pusher $150_a$) to contact and, subsequently, eject the associated set of surgical fasteners (e.g., set of surgical fasteners $130_a$) towards the depression 91 in the anvil 90 (FIGS. 4B and 4C). Each of the link assemblies 302 disengages from the engagement surfaces $154_a$, $162_a$ of the pusher and internal channel housing, respectively (FIG. 4D). The plurality of pivotably connected link assemblies 302 are transitionable from an initial position (FIG. 4A) through a subsequent position (FIGS. 4B and 4C) to a final position (FIG. 4D).

In the embodiment illustrated in FIGS. 4A-4D, the plurality of link assemblies 302 includes three link assemblies $302_a$, $302_b$, and $302_c$ (for illustration only). Each of the link assemblies 302 includes at least two link arms (e.g., a first link arm $304_a$ and a second link arm $308_a$). Each of link assemblies 302 is configured in a manner substantially similar to one another. For the purposes of brevity, and unless otherwise noted, the operative features of each of the link assemblies 302 is described hereinafter with reference to link assembly $302_a$. Link assembly $302_a$ includes a first link arm $304_a$ having a proximal end $306_a$ releasably engaged with a corresponding engagement surface $154_a$ associated with the pusher $150_a$ and a second link arm $308_a$ having a proximal end $310_a$ releasably engaged with a corresponding engagement surface $162_a$ associated with the internal channel housing 160. Each of the first and second link arms, $304_a$ and $308_s$, respectively, includes respective distal ends $312_a$ and $314_a$ pivotably coupled to each other. More particularly, in an embodiment, the distal ends $312_a$ and $314_a$ maybe coupled to each other to form a "living hinge" 178 therebetween (FIG. 4B) In an alternate embodiment, the distal ends $312_a$ and $314_a$ may be pivotably coupled to each other via a pivot pin, protrusion, or other suitable structure. The first and second link arms $304_a$ and $308_s$ extend from their respective distal ends 312, and $314_a$ toward their respective proximal ends 306a, 310a forming an angle $\alpha_s$ therebetween. Consequently, each of first and second link arms $304_a$ and $308_a$ is also angled with respect to an axis "C-C" defined through the cartridge 100 (FIG. 4A). Axis "C-C" extends parallel to the longitudinal axis "A". The angle $\alpha_s$ may range from acute to more than 180°. In one particular embodiment, angle $\alpha_s$ ranges from about 0° to about 179°.

Each link assembly 302 is operably coupled to one another via an activation structure 350 for transitioning each of the link assemblies 302. Activation structure 350 is adapted to operatively connect to a drive mechanism (e.g. movable handle 1002 and operative components associated therewith) associated with a surgical fastening apparatus 1000. The activation structure may be any suitable activation structure known in the art. In embodiments, the activation structure 350 for transitioning each of the link assemblies is selected from the group consisting of cable, wire, chain, flexible band or other elastic member, and rope. In the embodiment illustrated in FIGS. 4A-4D, the activation structure 350 is a pull cable 350 configured to transition each of the link assemblies 302 from the initial position to the final position when the cable 350 is "pulled" proximally. Thus, a "push" action that is typically employed with conventional surgical fastener applying apparatuses to move an associated conventional sled is replaced by this "pull" action that is independently disposed on each side of a DLU. This "pull" action minimizes firing forces and buckling of a driving mechanism. Cable 350 includes a plurality of cable segments 352 that includes cable segment $352_a$, $352_b$ and $352_c$ operably disposed between each of the link assemblies 302. More particularly, a cable segment $352_a$ operably connects to link assembly $302_a$ and a drive mechanism associated with the surgical fastener apparatus 100a, a cable segment $352_b$ operably connects to link assembly $302_b$ and link assembly $302_a$, a cable segment $352_c$ operably connects to link assembly $302_c$ and link assembly $302_b$, and so on. Each of the cable segments 352 (e.g., cable segment $352_a$ of the cable 350) is operably coupled to corresponding distal ends (e.g., distal ends $312_a$ and $314_a$ of the link arms $304_a$ and $308_a$, respectively). Cable segments 352 may be coupled to a link assembly 302 by any suitable methods. For example, in embodiments, cable segment 352 may be coupled to a link assembly 302 via an adhesive or the like. Other suitable structure(s) for coupling cable segment 352 to a link assembly 302 are contemplated. In the embodiment illustrated in FIGS. 4A-4D, each cable segment 352 includes an amount of initial slack "S". The amount of slack "S" is configured to facilitate sequential ejection of the surgical fasteners 130. More particularly, each cable segment 352 provides a predetermined time-delay from when one set of surgical fasteners 130 forms to the next. The amount of slack "S" may be varied to achieve desired time-delays. For example, in an embodiment, an amount of slack "S" associated with a cable segment increases from a proximal most cable segment, e.g., cable segment $352_a$, to a distal most cable segment, e.g., cable segment $352_c$. Alternatively, the amount of slack of each cable segment 352 may be uniform throughout the length of the cable 350. The specific slack "S" and/or time-delays associated with each of the cable segments 352 will depend on the contemplated uses of a manufacturer.

As noted above, both operable tools 1006 and 2006 including respective cartridges 100 and 200 may be configured for use with the firing mechanism 300. A distinctive feature of actuation mechanism 300 when used in the cartridge 200 as compared to cartridge 100 is a predetermined location of the actuation mechanism 300 (and operative components associated therewith) along a length of the cartridge 200. More particularly, in the instance where the cartridge 200 is employed with the operable tool 2006, the actuation mechanism 300 is operably positioned along a predetermined length of curvature of the cartridge 200. In any event, however, by implementing a firing mechanism 300 with the cartridges 100 and 200 and the respective operable tools 1006 and 2006, the need for a sled and/or a majority of operative components associated therewith is eliminated. The elimination of the sled and/or operative components associated therewith may prove advantageous during operation of the operable tools 1006 and 2006. More particularly, and as noted above, a "push" action that is typically employed with conventional surgical fastener applying apparatuses to move an associated conventional sled is replaced by a "pull" action that is independently disposed on each side of a DLU. This "pull" action minimizes firing forces and buckling of a driving mechanism. For example, the large firing force typically required for translating a sled through the operable tool 2006 is greatly reduced by the combination of link assemblies 302 and activation structure 350 of the present disclosure. More particularly, linkage system 302 of the actuation mechanism 300 may be operably disposed along a length of curvature of the operable tool 2006 thus reducing and/or eliminating the large firing forces required to "push" a sled along the same length. Moreover, the cost of manufacture associated with conventional cartridges (e.g., the multitude of individual components that require individual manufacture processes) is greatly reduced. That is, the links 302 including living hinge 178, break-away bridge, e.g., break-away bridge 170, and associated cable segments 352 of actuation mechanism 300 may be molded as one component (e.g., monolithically formed as a single component). This monolithic formation of the actuation mechanism 300 further facilitates in minimizing the size of conventional operable tools, e.g., operable tools 1006 and 2006.

In use, initially movable handle 1002 is in a distal position and each of the plurality of link assemblies 302, e.g., link assemblies $302_a$, $302_b$ and $302_c$, is in the position shown in FIG. 4A. More particularly, each of the respective proximal and distal ends of the link assemblies $302_a$, $302_b$ and $302_c$, is operatively engaged with the break-away bridges 170 of the bottom and top engagement surfaces of the pushers 150 and channel 160, respectively. When cable 350 is "pulled" (e.g., movable handle 1002 is moved proximally through a firing sequence) in the direction indicated by directional arrow "F", cable segment $352_a$ causes link assembly $302_a$ to pivot about the arcuate surface $158_a$ of the pusher $150_a$ and arcuate surface of the proximal end 166, (FIG. 4B). As link assembly $302_a$ pivots, a corresponding pusher $150_a$ is forced vertically upward in the direction indicated by directional arrow "G" toward a corresponding surgical fastener $130_a$ (FIG. 4B). The amount of initial slack "S" between link assemblies $302_a$ and $302_b$ causes a time-delay before the link assembly $302_b$ is caused to pivot. More particularly, link assembly $302_b$ begins to pivot while the link assemblies 302 that are disposed distally relative to link assembly $302_a$ and link assembly $302_b$, e.g., link assembly 302, remain in an initial position. Once link assembly $302_a$ is in a vertical position (e.g., perpendicular to axes "A-A" and "C-C") and the corresponding set of surgical fasteners $130_a$ are formed within a corresponding anvil pocket, the initial slack "S" between the link assemblies $302_a$ and $302_b$ is no longer present and the cable segment $352_b$ becomes taut (FIG. 4C). Additionally, when link assembly $302_a$ is in this vertical position, each of the sets of surgical fasteners 130, e.g., $130_b$ and $130_c$ is partially formed. In an embodiment, when the set of surgical fasteners $130_b$ is completely formed (i.e., link assembly $302_1$, is in a vertical position) and the set of surgical fasteners $130_c$ is partially formed, the link assembly $302_a$ is caused to disengage from the break-away bridges 170 associated with the engagement surface $154_a$ of the pusher $150_a$ and engagement surface $162_a$ of the top surface 164 (FIG. 4D). The foregoing sequence of events is perpetuated throughout the plurality of link assemblies 302 and corresponding cable segments 352 as the cable 350 is "pulled" proximally, which, in turn causes a "wave" of sets of surgical fasteners 130 to form toward a distal end of the cartridge 100.

Figure 6A:
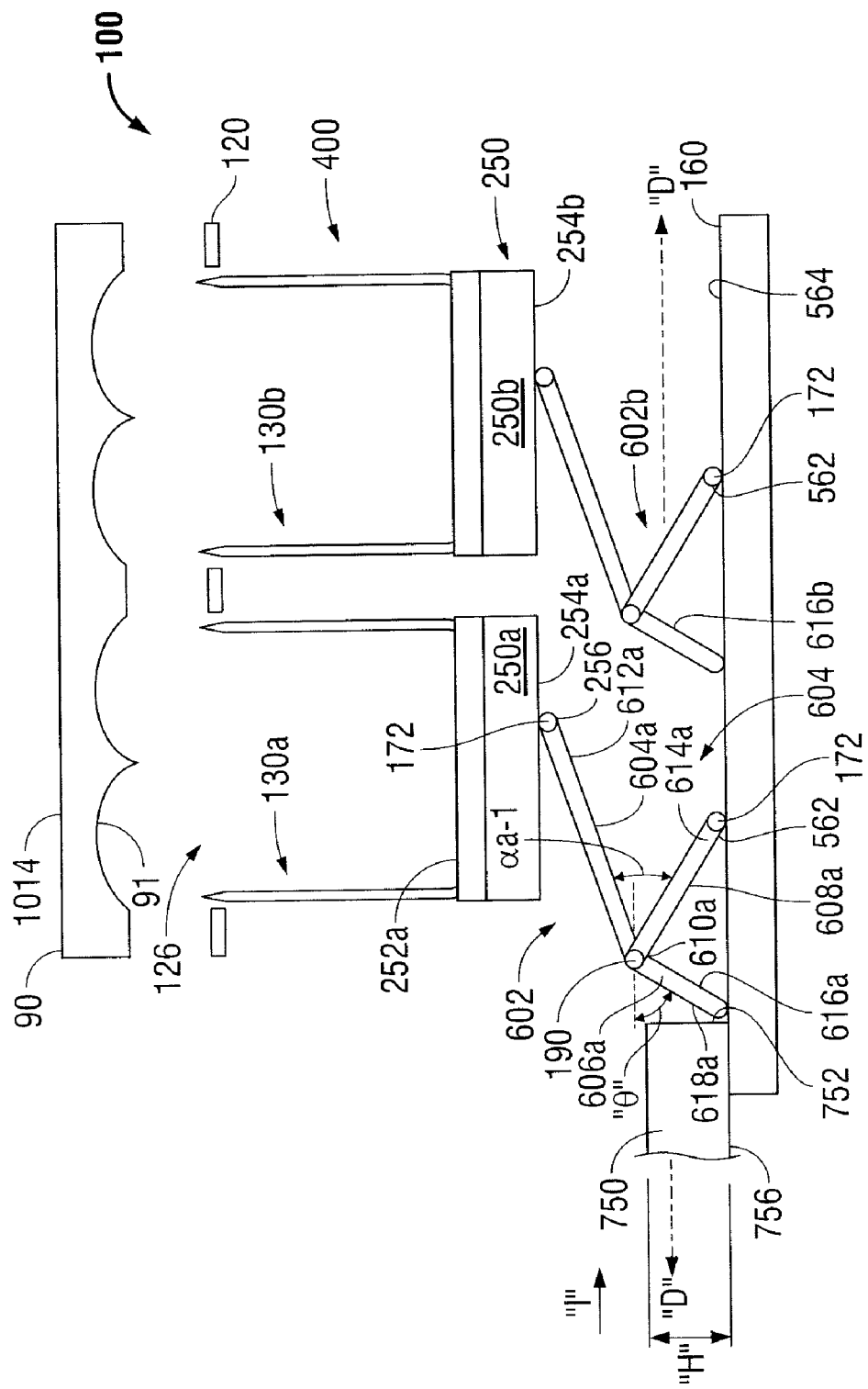
FIGS. 6A-6D are enlarged partial side views of a surgical fastener cartridge intended for use with the surgical fastener applying apparatuses illustrated in FIGS. 1 and 2 with the actuation mechanism shown in various positions during operation in accordance with an alternate embodiment of the present disclosure.

With reference to FIGS. 6A-6D, and initially with reference to FIG. 6A, an alternate embodiment of an actuation mechanism is shown designated 400. Actuation mechanism may be employed with both of the cartridges 100 and 200. As noted above, the structural and functional features of the cartridges 100 and 200 are substantially equivalent. Thus, for the purposes of brevity, and so as not to obscure the present disclosure with redundant information, the structural and functional features of cartridges 100 and 200 will be described hereinafter with reference to cartridge 100. Cartridge 100 will be described in terms of use with the surgical fastener applying apparatus 1000 and the operative tool 1006 of FIG. 1. Unless otherwise noted, it is assumed that the description that follows herein applies equally to the cartridge 200 and operative tool 2006. The features unique to cartridge 200 and operative tool 2006 will be described hereinafter only to the extent necessary to facilitate understanding of the present disclosure.

Actuation mechanism 400 may be operably housed within the cartridge body 112 and is configured to sequentially eject the plurality surgical fasteners 130 from the cartridge body 112 toward the anvil 90. To this end, in the embodiment illustrated in FIGS. 6A-6D, the internal channel housing 160 may be defined by and operably disposed (e.g., grounded) within the cartridge body 112 on opposite sides of the channel 122. Channel housing 160 is operably disposed adjacent a bottom portion of the cartridge body 112. In the embodiment illustrated in FIGS. 6A-6D, the channel housing 160 extends along a length of the cartridge body 112 and includes a top surface 564 having a plurality of pivots 562 disposed at predetermined locations along the top surface 564 of channel housing 160. Each of pivots 562 is in operative alignment with each of the first, second, and third rows 128$_A$, 128$_B$, 128$_C$, respectively, of the cartridge 100 for ejecting a corresponding set of surgical fasteners 130. The plurality of pivots 562 is configured to pivotably retain a portion of a corresponding linkage or link member 602. More particularly, pivots 562 include a pivot pin 172 that pivotably connects to a corresponding link member 602. In embodiments, each of the pivot points 562 may be monolithically formed with the top surface 564 of the channel housing 160 or a separate component attached by suitable structure.

With continued reference to FIG. 6A, actuation mechanism 400 includes a plurality of pushers 250. So as not to obscure the present disclosure with redundant information, the actuation mechanism 400 is described in terms of use with two (2) pushers 250. In the embodiment illustrated in FIGS. 6A-6D, pushers 250 include pusher 250$_a$ and 250$_b$. As described above with respect to pushers 150, pushers 250 are operably associated with a corresponding set of the surgical fasteners 130. More particularly, a pusher 250$_a$ is operably associated with a set of surgical fasteners 130$_a$ and a pusher 250$_b$ is operably associated with a set of surgical fasteners 130$_b$. For the purposes of brevity, and unless otherwise noted, the operative features of pushers 250 and corresponding sets of surgical fasteners 130 is described hereinafter with reference to a pusher 250$_a$ and corresponding set of surgical fasteners 130$_a$. Pusher 250$_a$ is configured similarly to pusher 150$_a$. More particularly, pusher 250$_a$ is configured to eject the corresponding set surgical fasteners 130$_a$ towards a depression, e.g., a depression 91, in an anvil. With this purpose in mind, a pusher 250$_a$ includes a surgical fastener contacting top surface 252$_a$ in vertical registration with the set of surgical fasteners 130$_a$. Top surface 252$_a$ is dimensioned to contact each of the surgical fasteners 130 in the set of surgical fasteners 130$_a$. Thus, when pusher 250$_a$ is caused to move upward, a surgical fastener 130 in the set of surgical fasteners 130$_a$ is simultaneously ejected through a respective first, second, and third rows 128$_A$, 128$_B$, 128$_C$. Top surface 252$_a$ includes a generally flat configuration that allows the surgical fasteners 130 in the set of surgical fasteners 130$_a$ to form a staple line that is uniform, i.e., a hemostatic effect associated with each of the formed surgical fasteners 130 is uniform across the staple line. As with top surface 152, of pusher 152, top surface 252$_a$ may include one or more protuberances or grooves 156 configured to vary a height of the top surface 252$_a$ such that the surgical fasteners 130 in the set of surgical fasteners 130$_a$ form a staple line that is non-uniform, i.e., a hemostatic effect associated with each of the formed surgical fasteners 130 is non-uniform across the staple line. For example, in an alternative embodiment, a surgical fastener formed closer to the channel 122 provides a greater hemostatic effect to stapled tissue than a surgical fastener formed further from the channel 122.

Pusher 250$_a$ includes a bottom surface 254$_a$ that includes a pivot 256 located at a predetermined position along the bottom surface 254$_a$. In the embodiment illustrated in FIGS. 6A-6D, pivot 256 is offset with respect to the pivot 562 positioned on the top surface 564. This configuration of a pivot 256 and pivot 562 that are offset with respect to each other facilities pivoting of the link member 602, which, in turn, facilitates ejecting a corresponding set of surgical fasteners 130. Alternatively, pivot 256 and pivot 562 may be disposed in vertical registration with respect to each other. Pivot 256 includes to a pivot pin 172 (FIG. 6B) that pivotably connects to a corresponding link member 602. In embodiments, each of the pivots 256 may be monolithically foil ied with the bottom surface 254$_a$ of pusher 250$_a$ or a separate component attached by suitable structure. In embodiments, the pivot 256 may be disposed within or operatively associated with an arcuate portion associated with the bottom surface 254$_a$, such as, for example, the arcuate portion located adjacent the proximal end 158$_a$ of bottom surface 154$_a$.

The actuation mechanism 400 includes a plurality of pivotably connected link members 602. In the embodiment illustrated in FIGS. 6A-6D, the plurality of link members 602 includes two link members 602$_a$ and 602$_b$ (see FIG. 6B, for example). Each of the link members 602 includes at least two link fingers 604. Each of link members 602 is configured in a manner substantially similar to one another. For the purposes of brevity, and unless otherwise noted, the operative features of each of the link members 602 is described hereinafter with reference to a link member 602$_a$. Link member 602$_a$ includes a first link finger 604$_a$ having a proximal end 606$_a$ pivotably coupled to a proximal end 610$_a$ of a second link finger 608$_a$. More particularly, a pivot pin 190 (or other suitable structure configured to provide a point of pivot) pivotably couples each of first and second link fingers 604$_a$ and 608$_a$ to one another. Each of the respective first and second link fingers, 604$_a$ and 608$_a$ includes a respective distal end 612$_a$ and 614$_a$. Distal end 612, pivotably couples to pivot 256 of the pusher 250$_a$. Likewise, distal end 614$_a$ pivotably couples to pivot 562 positioned on top surface 562$_a$. The first and second links 604$_a$ and 608$_s$ extend from their respective distal ends 612, and 614, toward their respective proximal ends 606a, 610a foilning an angle $\alpha_{a-1}$ therebetween. Consequently, each of first and second link fingers 604$_a$ and 608$_a$ is also angled with respect to an axis "D-D" defined through the cartridge 100. The angle $\alpha_{a-1}$ may range from acute to more than 180°. In one particular embodiment, angle $\alpha_{a-1}$ ranges from about 0° to about 179°. First link finger 604$_a$ and second link finger 608$_a$ are laterally spaced apart or offset from each other and configured such that only the first link finger 604$_a$ contacts the activation mechanism 750 when the activation mechanism is translated distally through the cartridge 100 (see FIG. 6C in conjunction with FIG. 7).

Figure 6B:
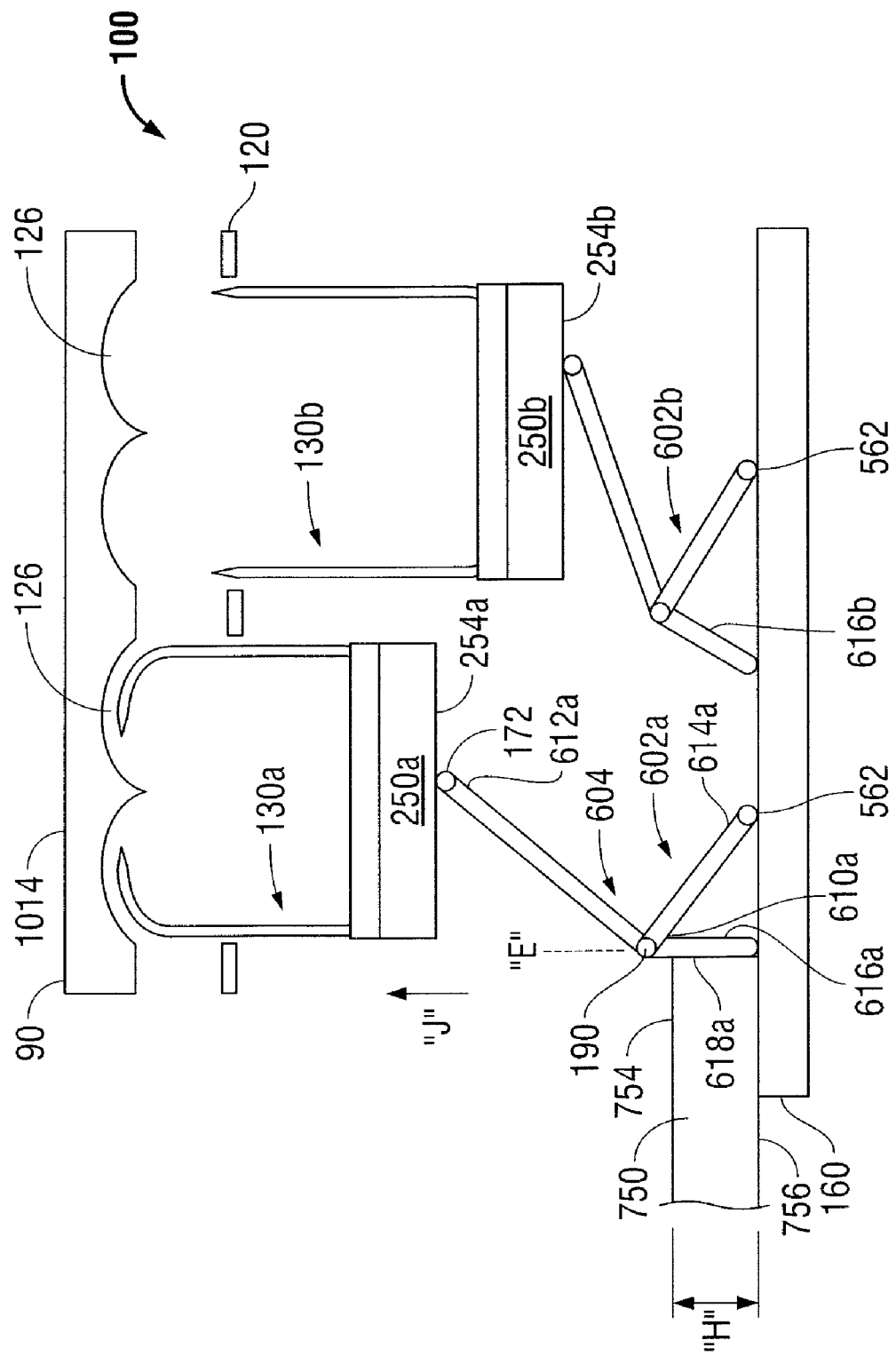
Figure 6C:
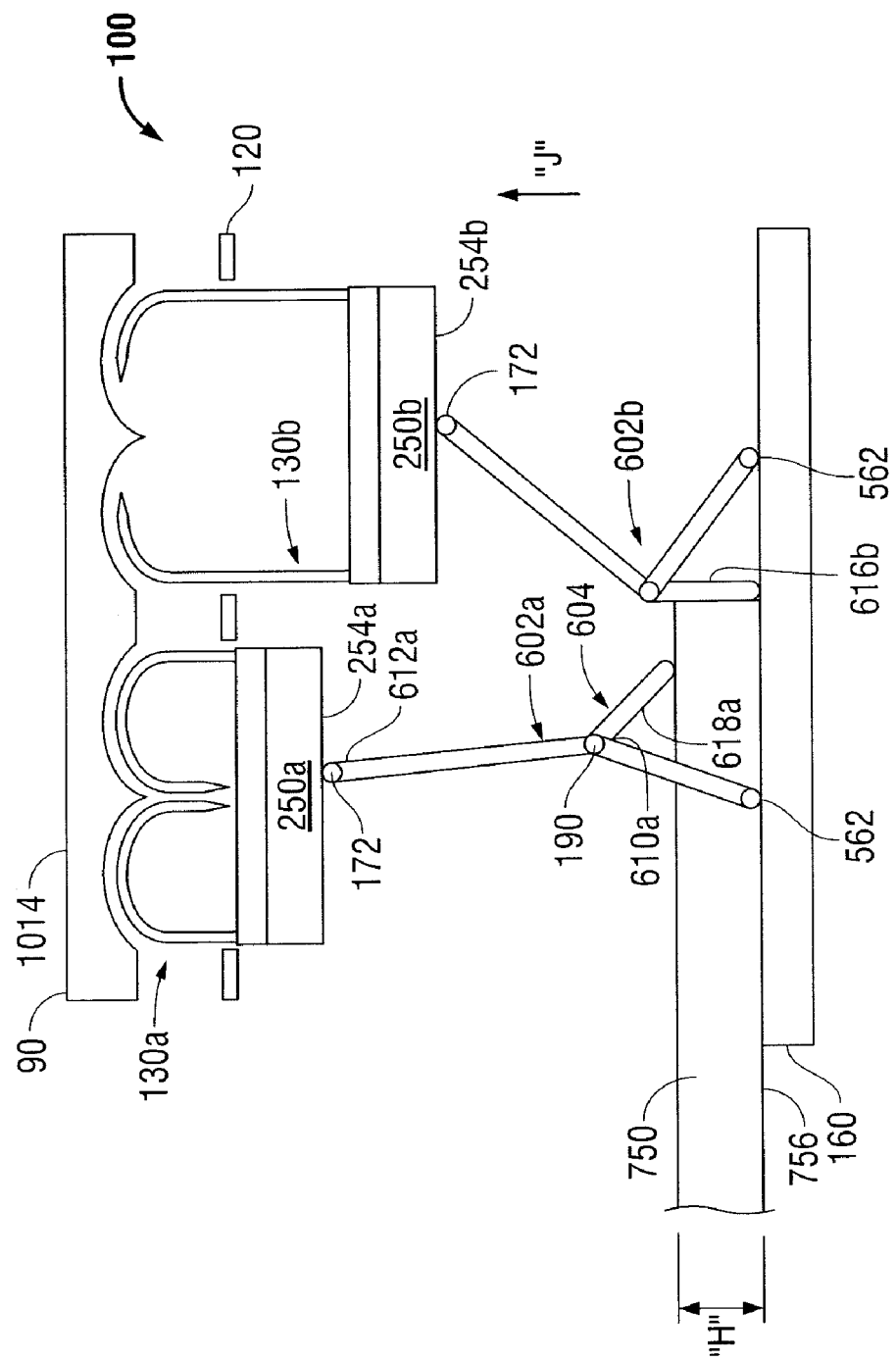
Figure 6D:
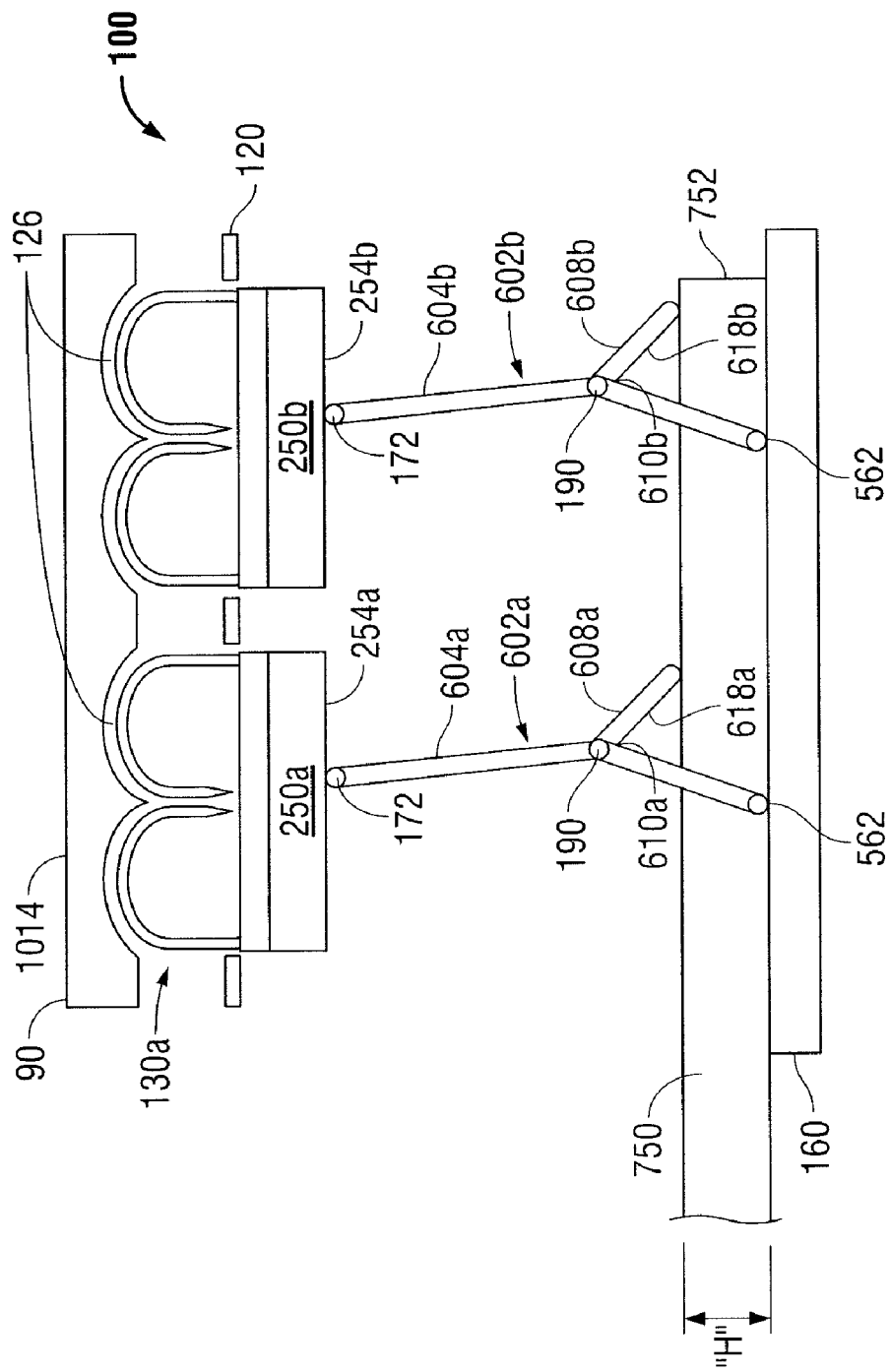
Figure 6E:
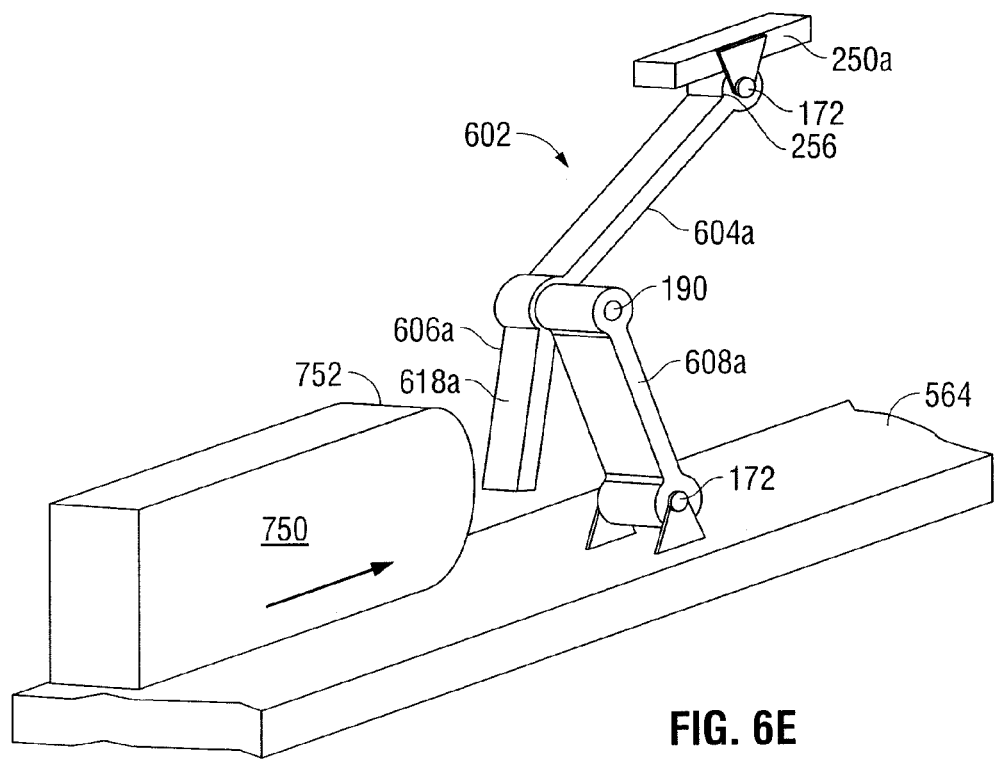
FIG. 6E is a perspective view of the actuation mechanism depicted in FIGS. 6A-6D shown in an initial position and with a drive rod according to an embodiment of the present disclosure.
Figure 7:
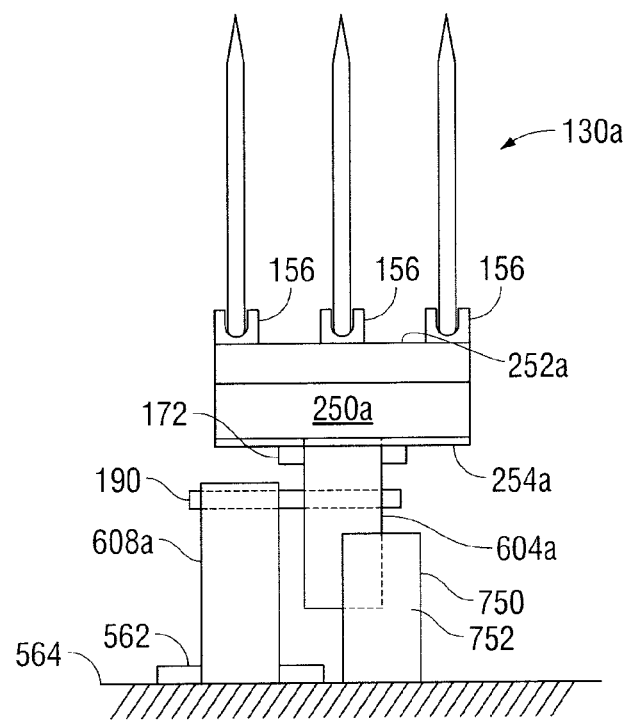
FIG. 7 is a cut-away view of the surgical fastener cartridge depicted in FIGS. 6A-6D.

Link member 602$_a$ includes a lower portion 616$_a$ that extends from the proximal end 606$_a$ of the first link finger 604$_a$ (as best seen in FIG. 6E). Lower portion 616, is configured to operatively contact a portion of an activation structure 750 when the activation structure 750 is moved distally. More particularly, the lower portion 616, includes a generally flat contacting surface 618$_a$ that is configured to contact a distal contacting surface 752 of the activation structure 750 (FIG. 6B). The flat surface 618$_a$ is configured to provide a smooth pivotable transition for the link member 602$_a$ when the activation structure 750 is moved distally through the cartridge 100. The lower portion 616, of the proximal end 606$_a$ of the first link member 602$_a$ may extend from the proximal end 606$_a$ toward the top surface 564 of channel 160 at an angle θ that ranges from about 0° to over 180° (FIG. 6A). In the embodiment illustrated in FIGS. 6A-6D, the lower portion 616, extends from the proximal end 606$_a$ at an angle θ that is with respect to the axis "D-D" and with respect to a plane "E-E" (FIG. 6B) that extends along the distal contacting surface 752 of the activation structure 750. Altering the angle between consecutive lower portions, e.g., between lower portion 616$_a$ and a lower portion 616$_b$ associated with link member 602$_b$, in combination with altering the contacting surface 618$_a$ and/or bottom surface 254$_a$ of pusher 250$_a$ may facilitate in obtaining a specific time-delay or specific hemostatic effect to tissue between subsequent formations of the surgical fasteners 130. For example, the lower portion 616$_a$ may extend in a manner as shown in FIGS. 6A-6D (i.e., at an angle that is ≈45°) and the lower portion 616$_b$ may extend at an angle θ that is less than the angle associated with the lower portion 616$_a$. For example, the lower portion 616$_b$ may extend at an angle that is ≈15°. In this instance, the distal contacting surface 752 of the activation structure 350 contacts the lower portion 616$_b$ for a longer period of time, which, in turn, may provide greater compression to the pusher 250$_a$ and/or a corresponding set of surgical fasteners 130$_a$.

Activation structure 750 for transitioning each of the link members 602 is adapted to operatively connect to a drive mechanism (e.g. movable handle 1002 and operative components associated therewith) associated with a surgical fastening apparatus 1000. In the embodiment illustrated in FIGS. 6A-6D, the activation structure 750 is a flexible or elastic drive rod 750. Drive rod 750 may have any suitable shape including but not limited to flat, curved angled, etc. In the embodiment illustrated in FIGS. 6A-6D, drive rod 750 includes a generally flat configuration having a generally rectangular shape and includes proximal and distal ends 754 and 756, respectively. In one particular embodiment, drive rod 750 may include a generally curved configuration having a generally circular shape, as best seen in FIG. 6E. Drive rod includes a height "H" that is less than the height of the power portion 616, (FIG. 6A). Proximal end 754 operatively couples to the drive mechanism of the surgical fastener applying apparatus 1000. As noted above, drive rod 750 includes distal contacting surface 752. Contacting surface 752 is located adjacent distal end 756 and includes a generally flat configuration. Alternatively, contacting surface 752 may include an arcuate, curved or slanted configuration. During a firing sequence of the surgical fastener applying apparatus 1000, drive rod 750 is translated distally through the cartridge 100 and sequentially contacts a respective lower portion, e.g., lower portion 616$_a$ of each of the link members 602. With this purpose in mind, the drive rod 750 is offset from each of the second link fingers, e.g., second link finger 608$_a$, associated with each of the link members 602 and is in-line with each of the first link fingers, e.g., first link finger 604$_a$, of the link members 602, such that during distal translation of the drive rod 750 through the cartridge body 100, each of the lower portions, e.g., lower portion 616$_a$, of the first link, e.g., first link finger 604$_a$ is caused to move from an initial position, wherein the lower portion 616$_a$ of the first link finger 604$_a$ is distal relative to the distal end 756 of the drive rod 750 and inside the path of translation of the drive rod 750 to a final position wherein the lower portion 616, of the first link finger 604$_a$ is proximal relative to the distal end 756 of the drive rod 750 and outside the path of translation of the drive rod 750.

As noted above, both operable tools 1006 and 2006 including respective cartridges 100 and 200 may be configured for use with the firing mechanism 400. A distinctive feature of actuation mechanism 400 when used in the cartridge 200 as compared to cartridge 100 is a predetermined location of the actuation mechanism 400 (and operative components associated therewith) along a length of the cartridge 200. More particularly, in the instance where the cartridge 200 is employed with the operable tool 2006, the actuation mechanism 400 is operably positioned along a predetermined length of curvature of the cartridge 200. In any event, however, by implementing a firing mechanism 400 with the cartridges 100 and 200 and the respective operable tools 1006 and 2006, the need for a sled and/or a majority of operative components associated therewith is eliminated. The elimination of the sled and/or operative components associated therewith may prove advantageous during operation of the operable tools 1006 and 2006. More particularly, by replacing the sled with an elastic drive rod 750 and set of links minimizes firing forces and buckling of a driving mechanism. For example, the large firing force typically required for translating a sled through the operable tool 2006 is greatly reduced by the combination of link members 602 and elastic drive rod 750 of the present disclosure. More particularly, link members 602 of the actuation mechanism 400 may be operably disposed along a length of curvature of the operable tool 2006 thus reducing and/or eliminating the large firing forces required to "push" a sled along the same length. Moreover, the cost of manufacture associated with conventional cartridges (e.g., the multitude of individual components that require individual manufacture processes) is greatly reduced. That is, the link members 602 of actuation mechanism 300 may be molded as one component (e.g., monolithically formed as a single component). This monolithic formation of the actuation mechanism 400 further facilitates in minimizing the size of conventional operable tools, e.g., operable tools 1006 and 2006.

In use, initially movable handle 1002 is in a distal position and each of the plurality of link members 602, e.g., each of link members 602$_a$ and 602$_b$ is in the position shown in FIG. 6A. As drive rod 750 translates distally through the cartridge 100 (e.g., movable handle 1002 is moved proximally through a firing sequence) in the direction indicated by directional arrow "I" (see FIGS. 6A and 6E), contacting surface 752 contacts surface 618$_a$ of the first link finger 604$_a$ (FIG. 6B). As first link finger 604$_a$ pivots, a corresponding pusher 150$_a$ is forced vertically upward in the direction indicated by directional arrow "J" toward a corresponding set of surgical fasteners 130$_a$. Once the pusher 130, is in vertical most position and the corresponding set of surgical fasteners 130, are formed within a corresponding anvil pocket, the drive rod 750 slides under the lower portion 616$_a$ of the first link finger 604$_a$ and continues distally thought the cartridge 100 (FIG. 6C). The foregoing sequence of events is perpetuated throughout the plurality of link members 602 as the drive rod 750 is translated distally, which, in turn causes a "wave" of sets of surgical fasteners 130 to form toward a distal end of the cartridge 100 until all the remaining sets of surgical fasteners are formed.

From the foregoing and with reference to the various figure drawings, those skilled in the art will appreciate that certain modifications can also be made to the present disclosure without departing from the scope of the same. For example, it is contemplated that any of the aforementioned link assemblies, e.g., link assembly 302, may be manufactured via nanofabrication processes.

Although the illustrative embodiments of the present disclosure have been described herein with reference to the accompanying drawings, the above description, disclosure, and figures should not be construed as limiting, but merely as exemplary of various embodiments.

What is claimed is:
1. A surgical fastener cartridge comprising:
a cartridge body including a tissue contacting surface, the tissue contacting surface including a plurality of fastener retention slots, the cartridge body defining a longitudinal axis therethrough;
a plurality of surgical fasteners operatively disposed in the plurality of fastener retention slots; and
an actuation mechanism housed within the cartridge body, the actuation mechanism comprising:
a plurality of pushers operably associated with the plurality of surgical fasteners, each pusher configured for ejecting an associated surgical fastener towards a depression in an anvil;
an internal channel housing;

a plurality of pivotably connected link assemblies operably coupled to one another via an activation structure configured to apply a pull force along the longitudinal axis for transitioning each of the link assemblies, wherein the plurality of pivotably connected link assemblies are movable from an initial position where each of the link assemblies are engaged with a corresponding bottom surface associated with each of the pushers and a corresponding top surface associated with the internal channel housing, through a subsequent position where each of the link assemblies are configured to cause the corresponding pusher to eject the associated surgical fastener towards the depression in the anvil, and to a final position where each of the link assemblies are disengaged from the bottom and top surfaces of the pusher and internal channel housing, respectively, wherein each of the pushers and corresponding top surface associated with the internal channel housing includes an arcuate portion configured to releasably engage a respective proximal end of a first and second link arm associated with each of the plurality of pivotably coupled link assemblies.

2. A surgical fastener cartridge according to claim 1, wherein the internal channel housing is defined by and operably disposed within the cartridge body.

3. A surgical fastener cartridge according to claim 2, wherein each link assembly is releasably engaged with a corresponding bottom surface associated with each the pushers and a corresponding top surface associated with the internal channel housing.

4. A surgical fastener cartridge according to claim 1, wherein the activation structure is adapted to operatively connect to a drive assembly associated with a surgical fastening apparatus.

5. A surgical fastener cartridge according to claim 1, wherein the tissue contacting surface includes a knife slot configured to accommodate longitudinal movement of a cutting element.

6. A surgical fastener cartridge according to claim 1, wherein the arcuate portion associated with each of the pushers is disposed near the center of the pushers and is in vertical registration with a corresponding arcuate portion of the top surface of the internal housing.

7. A surgical fastener cartridge according to claim 1, wherein the activation structure for transitioning each of the link assemblies is selected from the group consisting of cable, wire, chain, flexible band and rope.

8. A surgical fastener cartridge according to claim 7, wherein the activation structure is configured to transition each of the link assemblies when the activation structure is pulled proximally.

9. A surgical fastener cartridge according to claim 1, wherein each of the link assemblies includes at least two link arms including a first link arm having a proximal end releasably engaged with a corresponding bottom surface associated with each of the pushers and a second link arm having a proximal end releasably engaged with a corresponding top surface associated with the internal channel housing, each of the first and second links including distal ends pivotably coupled to each other.

10. A surgical fastener cartridge according to claim 9, wherein each of the first and second links arms of the link assemblies are disposed an oblique relation relative to each other.

11. A surgical fastener cartridge comprising:
a cartridge body including a tissue contacting surface, the tissue contacting surface including a plurality of fastener retention slots;
a plurality of surgical fasteners operatively disposed in the plurality of fastener retention slots;
an actuation mechanism housed within the cartridge body, the actuation mechanism comprising:
a plurality of pushers operably associated with the plurality of surgical fasteners, each pusher configured for ejecting an associated surgical fastener towards a depression in an anvil;
an internal channel housing defined by and operably disposed within the cartridge body;
a plurality of pivotably connected link assemblies, each link assembly pivotably engaged with and removably coupled to a corresponding bottom surface associated with each the pushers and a corresponding top surface associated with the internal channel housing, each link assembly being operably coupled to one another; and
an activation structure for transitioning each of the link assemblies, wherein the activation structure is configured to sequentially cause each of the link assemblies to move through a succession of motions within the cartridge body, such that the link assemblies cause the corresponding pusher to contact and, subsequently, sequentially eject the associated surgical fastener towards the depression in the anvil,
wherein the link assemblies are caused to disengage from the corresponding bottom surface associated with each of the pushers as a result of a pull force that is provided by the activation structure to move the link assemblies through the succession of motions within the cartridge body.

* * * * *